United States Patent
Wei

(10) Patent No.: US 11,406,649 B2
(45) Date of Patent: Aug. 9, 2022

(54) TREATMENT OF UPPER AERODIGESTIVE TRACT DISORDERS AND COUGH

(71) Applicant: IVIEW THERAPEUTICS, INC., Doylestown, PA (US)

(72) Inventor: Edward T. Wei, Berkeley, CA (US)

(*) Notice: Subject to any disclaimer, the term of this patent is extended or adjusted under 35 U.S.C. 154(b) by 257 days.

(21) Appl. No.: 16/501,056

(22) Filed: Feb. 14, 2019

(65) Prior Publication Data

US 2020/0171058 A1 Jun. 4, 2020

Related U.S. Application Data

(63) Continuation-in-part of application No. 16/350,559, filed on Nov. 30, 2018.

(51) Int. Cl.
| | |
|---|---|
| *A61K 31/66* | (2006.01) |
| *A61P 11/14* | (2006.01) |
| *A61K 31/662* | (2006.01) |
| *A61K 9/00* | (2006.01) |
| *A61K 9/08* | (2006.01) |
| *A61K 47/26* | (2006.01) |
| *A61K 9/06* | (2006.01) |

(52) U.S. Cl.
CPC .......... *A61K 31/66* (2013.01); *A61K 9/0056* (2013.01); *A61K 9/06* (2013.01); *A61K 9/08* (2013.01); *A61K 47/26* (2013.01); *A61P 11/14* (2018.01)

(58) Field of Classification Search
None
See application file for complete search history.

(56) References Cited

U.S. PATENT DOCUMENTS

| | | | |
|---|---|---|---|
| 2015/0111852 A1* | 4/2015 | Wei | A61P 15/00 514/75 |
| 2015/0164924 A1* | 6/2015 | Wei | C07F 9/5304 424/443 |

* cited by examiner

*Primary Examiner* — Bethany P Barham
*Assistant Examiner* — Peter Anthopolos

(57) ABSTRACT

The present discovery pertains generally to the field of therapeutic compounds. More specifically the present discovery pertains to a particular 1-di-alkyl-phosphinoyl-alkane, 1-(Diisopropyl-phosphinoyl)-nonane, referred to herein as "DIPA-1-9". Surprisingly and unexpectedly, DIPA-1-9, is able to selectively treat (e.g., suppress) sensory discomfort arising from the lumenal epithelial lining of the pharynx and esophagus without side effects. Compared to structurally similar compounds, DIPA-1-9 did not have the problems of painful cold, stinging, or irritancy, or of adverse taste when applied in the oral cavity. To deliver the DIPA-1-9 to the lumenal epithelium of the pharynx and esophagus, an ideal formulation for delivery is a solution of DIPA-1-9 in syrup, at a concentration of 5 to 12 mg/mL and a delivery volume of less than 1 mL. The delivery unit can be a plastic vial with a design such that the syrup is poured onto the base of the tongue, next to the pillars of fauces. The DIPA-1-9 then reaches the nerve endings at the base of the epithelia and transduces signals of coolness and cold. Cooling of the pharyngeal and esophageal lining relieves discomfort and is useful for conditions such as throat irritation, pharyngitis, tonsillitis, cough, chronic cough, heartburn, chest pain, and esophagitis. Moreover, the elicitation of cooling in the pharynx and esophagus can be utilized to treat dysphagia, dyspepsia, and dyspnoea, and to enhance mucus expectoration in inflammatory airway disorders such as cystic fibrosis, asthma, and chronic obstructive pulmonary diseases (which includes bronchitis and bronchiectasis). A particularly preferred embodiment is DIPA-1-9 dissolved in a syrup vehicle in a delivery unit volume of less than 1 mL.

15 Claims, 8 Drawing Sheets

DIPA-1-9 in Syrup

TREATMENT OF UPPER AERODIGESTIVE TRACT DISORDERS AND COUGH

CROSS-REFERENCE TO RELATED APPLICATIONS

Figure 1:
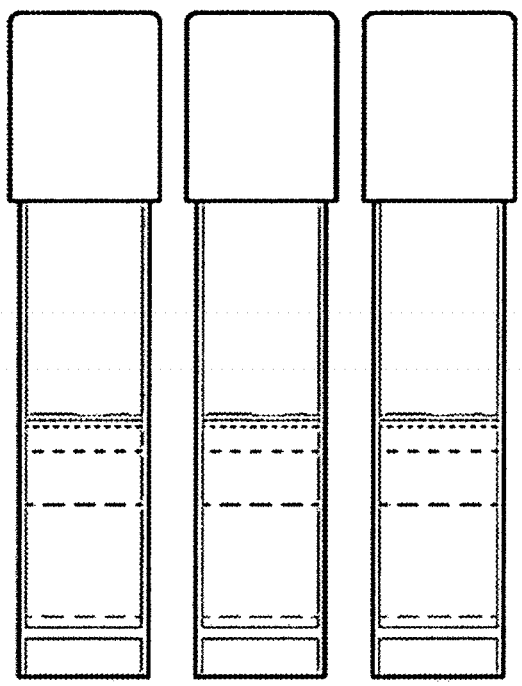

This application is a continuation-in-part of Ser. No. 16/350,559, filed on Nov. 30, 2018.

BACKGROUND OF THE INVENTION

The US FDA identifies a new medicine as "First-in-Class" when the drug uses a new and unique mechanism of action for treating a medical condition. First-in-Class designation is one indicator of the innovative nature of a drug. For a molecule to succeed as a drug, it is necessary to define the medical condition precisely and to choose the right mechanism of action, the right molecule, the right place (target) for delivery, a delivery system to deliver the right dose at the target site, and to deliver the molecule at the right time. If any of these parameters fail, the new medicine will not work. No new medication has been introduced in the past 50 years for the treatment of upper aerodigestive tract discomfort such as cough, dysphagia or dyspnea, so success in treatment of the proposed strategy will indicate innovation.

A number of publications are cited herein in order to more fully describe and disclose the discovery and the state of the art to which the discovery pertains. Each of these publications is incorporated herein by reference in its entirety into the present disclosure, to the same extent as if each individual publication was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present discovery. It is not an admission that any of the information provided herein is prior art or relevant to the presently claimed invention, or that any publication specifically or implicitly referenced is prior art.

Medications and Target Surfaces of the Upper Aerodigestive Tract

The lumen of the aerodigestive tract is a common conduit for food, liquid, and air, and is part of both the digestive and respiratory systems. This tract is composed of the mouth, pharynx, larynx, and parts of the esophagus. In laymen's terms it includes the organs and tissues of the lips, mouth, tongue, throat, vocal cords, and parts of the esophagus and windpipe. The traffic that passes through this tract every day is astounding. On an average day, an adult breathes 12,000 L of air, drinks 2 L of fluids, secretes 1 L of saliva, and eats 2 kg of food. These activities are constant, with about 15 breaths and 1 swallowing movement per min during the waking hours. For survival, the traffic flow must be co-ordinated so that food and liquids go down the esophagus and not into the airways, and air gets directed into the airways. The efficiency of this system is visible and self-evident, for example, when a large pizza is consumed with a soft drink. The transit of mass from mouth to stomach is accomplished with a minimum of fuss with the subject breathing at the same time.

The aerodigestive tract lining is susceptible to injury because of exposure to physical, chemical, and biological agents. Refluxed digestive enzymes and acids, infectious agents such viruses, and nasally secreted and airways secreted exudates can all injure the lining, cause inflammation, and produce discomfort and pain. One common pathway for the expression of discomfort, as the aerodigestive tract attempts to get rid of the irritant.

There are currently two types of drugs for the aerodigestive tract. One is local anesthetics, such as procaine and lidocaine, which inhibit nerve conduction of nociceptive signals towards the central nervous system. Lidocaine can be applied via a lozenge to diminish the discomforts of a sore throat (pharyngitis). But local anesthetics have the undesirable property of numbing the tissues to touch and pressure. Prolonged use is dangerous because this class of drugs can cause hypersenstivity reactions and may interfere with wound healing. Narcotic analgesics, such as morphine and codeine, have long been used to treat cough. Dextromethorphan and codeine are "centrally-acting antitussives", i.e. they act on elements in the brain or spinal cord to suppress cough. Dextromethorphan, in most individuals, is rapidly metabolized after "first-pass" absorption via the gastrointestinal tract. Hence, it must be taken 3 or 4 times a day to maintain an adequate plasma level. Dextromethorphan is used in over 150+ over-the-counter preparations for cough. Codeine is a narcotic analgesic (Schedule 3 drug) that can only be obtained by prescription. Both codeine and dexthromethorphan are subject to abuse. The efficacy of dextromethorphan and codeine in suppressing cough has been questioned. In double-blind, placebo-controlled studies, both drugs were not better than placebo.

First generation antihistamines, such as Benadryl® (diphenhydramine) and Chlortrimeton® (chlorpheniramine) have a drying effect on nasal secretions which are sometimes beneficial for cough associated with the common cold and allergies. These compounds also have a sedative, depressive action on the brain. Antihistamines are not effective for dry hacking coughs seen, for example, in flus or asthma. Side-effects such as sedation and dry mouth limit their use for the treatment of cough.

Guaifenesin is an "expectorant" which means it promotes the secretion and "thinning" of mucus on the surface of the airways. The efficacy of guaifenensin in various forms of cough has not been established in placebo-controlled, double-blind studies. Guaifenesin is an ingredient in many generic products. Hypersecretion of mucus is contraindicated in certain coughing patients with asthma or chronic obstructive pulmonary disease (COPD) and guaifenesin should not be used in such patients.

Menthol and related monoterpenes have some limited analgesic action and are used in lozenges and confectionery for sore or irritated throats and for cough. Menthol cough drops or lozenges typically weigh about 3.4 g (Walgreens cough drops) or 2.7 g (N'Ice lozenges) and contain from 5, 7, or up to a maximum of 10 mg of (−)-menthol in a sugar-dye matrix. Doses of menthol higher than 7 mg do not sell because the harsh taste of (−)-menthol makes the lozenge unpalatable. Also, when doses of 5 mg menthol enter the esophagus, an unpleasant cold is felt behind the sternum. The menthol lozenges are held in mouth for about 10 to 15 min and soothe the lining of the mouth and the throat. The menthol lozenge may work well in cough not because of cooling but because if the lozenge is held in the mouth the sweetness exerts a pharmacological effect and the saliva generated must be swallowed. The act of swallowing evokes reflexes that inhibit coughing. A drawback to long term use of lozenges is the addition of sugar and calories to the diet.

A number of menthol-related compounds with physiological cooling effects on keratinized epithelia such as the skin and the tongue have been described by Watson et al. ["Compounds with the Menthol Cooling Effect", *J. Soc. Cosmet. Chem.* 29: 185-200, 1978]. Some of the compounds are used as additives to toothpaste, cosmetics, and comestibles, but none are used for the medical treatment of the aerodigestive tract. Trialkylphosphine oxides having a "physiological cooling action" were described [Rowsell et al. "Phosphine oxides having a physiological cooling effect", U.S. Pat. No. 4,070,496, 1978]. These compounds were not developed for use. Wei has proposed use of certain water-insoluble cooling agents for the treatment of cough (U.S. Pat. Nos. 8,426,463 and 8,476,317), but these agents are not easily formulated for delivery to nerve endings of the oropharynx. Recent research has focused on drugs that antagonize certain purinergic receptors located on vagal afferents. These new drug candidates must be administered via the bloodstream to reach the $10^{th}$ nerve endings in the airways.

Cough is a reflex designed to remove sensory irritants and obstructions from the airways. The origin of the stimuli for cough is generally thought to come from the laryngeal receptors located on afferents of the internal superior laryngeal nerve (ISLN), a branch of the vagus ($10^{th}$ cranial nerve), although the actual sites of inflammation that generates the cough signals to stimulate the ISLN afferents may originate from the nasopharynx, oropharynx, hypopharynx, esophagus and bronchi. Coughing is a familiar experience and is executed by a coordinated contraction of the respiratory muscles against a closed glottis. The causes of airway irritation and obstruction that lead to cough are multifactorial and include conditions such as viral or bacterial upper airway infections, post-nasal drip, allergies, inflammation of the airways from air pollutants, pharyngitis, laryngitis, and for chronic coughing such conditions as asthma, chronic obstructive lung disease, gastroesophageal reflux disease, lung cancer, pneumonia, sleep apnea, snoring, pulmonary edema, congestive heart failure, and dyspnea.

Current medications for coughing have limited efficacy, as witnessed by individuals who stay awake at night, unable to sleep because of cough, and individuals who cough for prolonged periods, for example, for 3 weeks after a viral infection of the upper airways. There is need for a new medication, simply applied, that will control cough for at least three to four hours to allow the patient to stop coughing and go to sleep. The new agent must have a rapid onset of action, of less than several minutes, to encourage patient adherence. It must be easy to administer and suppress sensory discomfort from the aerodigestive tract without aversive tastes, irritancy, pain, or toxicity. The drug is preferably topically applied and acts locally on the target nerve endings, and must also have a sufficient duration of action to be clinically meaningful.

The surfaces of the aerodigestive tract are covered by two types of epithelia. When the layer is one cell thick, it is called simple epithelium, and the respiratory epithelium of the nasopharynx, larynx, and trachea is a single layer. If there are two or more layers of cells, it is called stratified epithelium. Stratified epithelium are composed mainly of squamous (flattened) cells and some cuboidal cells and cover the pharyngeal surface and the oesophageal surface. The sensory nerve endings in the basal layer of the epithelia transduce the signals that are perceived as discomfort by the brain. As might be expected, drug penetration through the stratified epithelium is more difficult that access to the nerve endings of the simplified epithelium.

The dysesthesia arising from the aerodigestive tract differs from that of the skin. Note, for example, the sharp reaction of the laryngeal and tracheal membranes to distilled water; the choking sensations of chili pepper in the throat; the sour, acrid feeling of regurgitated acid in the back of the mouth and throat; the bilious nature of a full meal; the itch and urge to cough; the inability to breathe comfortably; and a throbbing sore throat. These sensations are clearly different from what can be felt from the skin, and each has their own characteristics. The nerve endings that report noxious signals from the aerodigestive tract originate mostly from the trigeminus ($5^{th}$), glossopharyngeus, ($9^{th}$) and vagus ($10^{th}$) nerves, and from some spinal sensory afferents of the esophagus. The targets for drug delivery are to the receptive fields of these nerve endings within the basal layers of the stratified epithelium. The proposed action of the drug of the preferred embodiment is to simulate the sensations of heat abstraction, that is, to cool.

About four decades ago, Watson et al. synthesized over 1200 compounds in an attempt to find cooling agents that had properties better than menthol [New compounds with the menthol cooling effect. J. Soc. Cosmet. Chem. 29: 185-200, 1978]. From this research, N-alkyl-cycloalkyl- and an N-alkyl-alkyl carboxamide, WS-3, WS-5, WS-12, and WS-23, were identified and used today as additives for confectionery, comestibles, (e.g., chewing gum), toothpaste and toiletries. These scientists also described phosphine oxides [Rowsell and Spring U.S. Pat. No. 4,070,496] with cooling properties. However, the phosphine oxides were not further investigated or commercialized.

Rowsell and Spring '496 tested the properties of cooling agents, including phosphine oxides, on volunteers by putting filter paper (1×1 cm), impregnated with a known amount of compound, onto the dorsal surface of the tongue of the test subject. After 30 sec, the subject was required to report presence or absence of a cooling effect. These data were reported as "Threshold, μg" and refer to the threshold amount of the test substance that produces cooling sensations upon application onto the tongue of a panel of human volunteers. The average threshold of (−)-menthol for 6 subjects was 0.25 μg, but there was a 100-fold variation in individual sensitivity. The surface of the tongue is keratinized. Cool signals detected from the dorsal surface of the tongue are often confounded by gustatory and olfactory variables.

The 1-dialkyl-phosphinoyl-alkanes are solvent-like molecules that require only several [1 to 3] steps for synthesis. They are also known as trialkylphosphine oxides, but the preferred term now is dialkyl-phosphinoyl-alkane or dialkylphosphorylalkane. Rowsell and Spring U.S. Pat. No. 4,070,496 described a range of phosphine oxides which have a physiological cooling effect on skin and on the mucous membranes of the body.

BRIEF SUMMARY OF THE INVENTION

For successful drug treatment of a medical condition, it is necessary to precisely define the medical condition and to choose the right mechanism of action, molecule, place for delivery, dose, and time of dosing to achieve successful therapy. Here, the medical condition treated is discomfort (irritation, itch, pain, dysesthesia) of the aerodigestive tract. Here, the medical condition treated is discomfort (irritation, itch, pain, dysesthesia) of the upper aerodigestive tract. Specifically, the section of the tract of interest is the oropharynx, hypopharynx (laryngopharynx), and the upper third of the esophagus. The right molecule is chosen from a set of agents that selectively and specifically cool (mimic the sensations of heat abstraction) without the adverse effects of bad taste or pain, and have a sufficient duration of therapeutic action. The right place for delivery is the nerve endings embedded in the stratified epithelium of the pharyngeal and esophageal epithelia. To achieve the right concentration, the molecule is preferably formulated in a syrup and topically applied. The volume of syrup is less than 1 mL per dose, and preferably less than 0.5 mL. The syrup used in this manner is a vehicle for focused delivery of the cooling ingredient to the oropharyngeal rim, at the base of the tongue next to the pillars of fauces, so that the active ingredient adheres to the wall of the orpharynx, hypopharynx, and upper third of the esophagus, and is not rapidly transferred into the lower esophagus. The syrup is not used here as a sweetener on the tongue, or as a vehicle for carrying active ingredients into the gastrointestinal tract. The taste buds for sweetness are in the front ⅓ of the tongue (anterior) whereas the placement of the syrup in this invention is in the back of the tongue (posterior). The time of delivery of the active ingredient dissolved in the syrup is selected when there is a need to relieve the discomfort and can be repeated without desensitization. One molecule is chosen from a set of agents that selectively and specifically cool (mimic the sensations of heat abstraction like a spoonful of Haagen-Dazs ice cream) without adverse effects of bad taste or pain. The targeted place for delivery is the nerve endings embedded in the stratified epithelium of the pharyngeal and esophageal epithelia. To achieve the right dose (which is concentration of the molecule×the volume delivered) the molecule is formulated so that it can be topically applied to and to quickly reach its target. This is achieved with a small volume (≤1 mL) of syrup applied to the base of the tongue. The time of delivery is chosen when there is discomfort and the onset of relief (≤1 min) can be immediate.

The present discovery pertains to one preferred di-alkyl-phosphinoyl-alkane called 1-(Diisopropyl-phosphinoyl)-nonane, referred to herein as "DIPA-1-9". Surprisingly and unexpectedly, DIPA-1-9, is able to treat (e.g., suppress) sensory discomfort from the upper aerodigestive tract selectively and specifically.

By selectivity, it is meant that DIPA-1-9 is first able to act on the TRPM8 receptor but not on TRPV1 or TRPA1 receptors, both of which are associated with perception of pain. Selectivity is also shown for DIPA-1-9 for pain thresholds, the hexyl and heptyl analogs produce "burning, icy cold" on the throat, but this is not seen with the nonyl DIPA-1-9. When compared to structurally similar compounds, selectivity was also found for comparisons of taste measurements on the tongue. DIPA-1-9 did not have significant adverse taste. Compounds with 6 to 8 carbons in the longest alkyl sidechain (hexyl, heptyl, and octyl) have organic metallic tastes.

By specificity, it is meant that DIPA-1-9 (and related analogs) activates the TRPM8 receptor with a range of potencies and full efficacy, as measured by the median effective dose ($EC_{50}$). The $EC_{50}$ potency is one aspect of specificity. The 95% confidence limits of the $EC_{50}$ has considerable overlap, so potency comparisons have limited value. TRPM8 receptor activation indicates cooling potential, but one cannot distinguish one analog versus another. On the other hand, another aspect of specificity called "efficacy" is of considerable importance for mechanism of action and for the selection of the right molecule. By efficacy is meant the maximal intensity of the desired pharmacological effect that is attainable. As described herein, DIPA-1-9 is able to evoke a cooling sensation on the pharyngeal and esophageal surfaces that is therapeutically comfortable and beneficial and which is not accompanied by adverse taste, pain or other undesirable sensations. The addition or removal of one methyl group from DIAP-1-9 abrogates these desirable qualities of efficacy. Consequently, DIPA-1-9 is efficacious, for example, in the treatment of multiple disorders (e.g., diseases) of discomfort from the upper aerodigestive tract, including oropharyngeal discomfort; esophageal discomfort; throat irritation; cough; dyspnea, dysphagia, heartburn; and chest pain of the upper aerodigestive tract. But the other analogs are not efficacious. The particular efficacious endpoint that is desired is the coolness that is similar to the sensations of a spoonful of a rich ice cream, such as Haagen-Dazs ice cream when swallowed, but longer-lasting.

Some of the contrasting specific actions of DIPA-1-9 versus for example DIPA-1-7 may be attributed to penetration of the molecule through cell layers. DIPA-1-7 permeates super-fast through cell barriers, and hence may activate pain receptors not accessible to DIPA-1-9. It is the selectivity and specificity of DIPA-1-9 that gives it unique attributes. Thus, the "right" molecule is identified.

The "right" dose (concentration×volume of delivery) of the efficacious molecule to activate the receptor is determined by method of drug delivery and physicochemical properties of the candidate molecule to penetrate barriers, and to reach the receptor. After delivery, the residence time of the molecule at the receptor is also a determinant of the "right" concentration. The key structural modifications in the preferred embodiment, DIPA-1-9, is the diisopropyl substitution and the extension of the longest alkyl chain to nine carbons (nonyl). This was learned by experiment. The DIPA-1-9 is 10× more water soluble than those of the prior art, and the nonyl substitution prolongs activity relative to the hexyl or heptyl analogs. The water solubility allows complete miscibility with the polar carrier vehicle (syrup) and facilitates delivery.

Another aspect of the present discovery pertains to use of DIPA-1-9 in the manufacture of a medicament for treatment of diseases, as described herein. The diisopropyl configuration makes the molecule achiral whereas the analogs described in Rowsell and Spring ('496) were 95% chiral. The nonyl substitution increases the duration of activity relative to the hexyl and heptyl analogs. A person skilled in the art who examined the prior art would not have routinely noticed the absence of information of the diisopropyl analogs, or be motivated to synthesize and test DIPA-1-9. It would have been difficult to predict the dramatic change in water solubility. Furthermore, it would not have been possible to predict, to infer, or to find that extension of the longest chain to the nonyl group will make significant differences in optimization of selectivity (in pain and in taste), of specificity (the right degree of cold), and of the duration of action.

Figure 2:
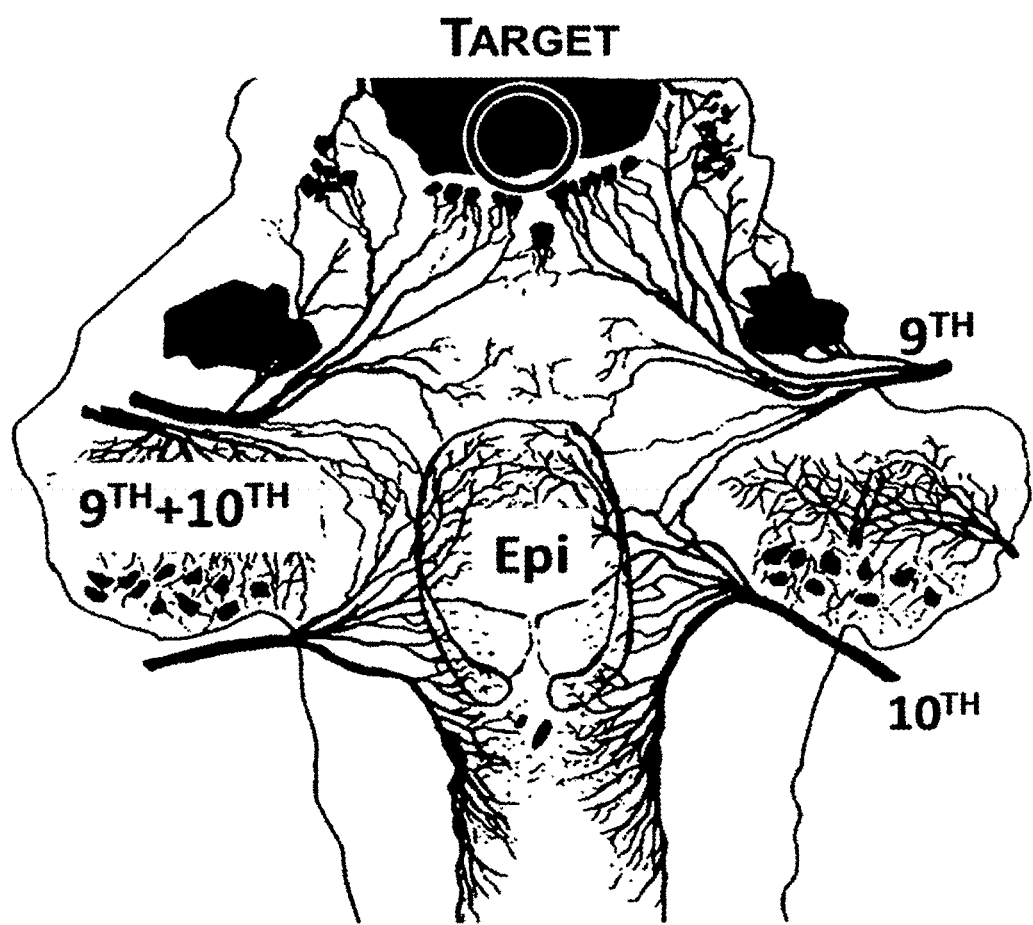
Figure 3:
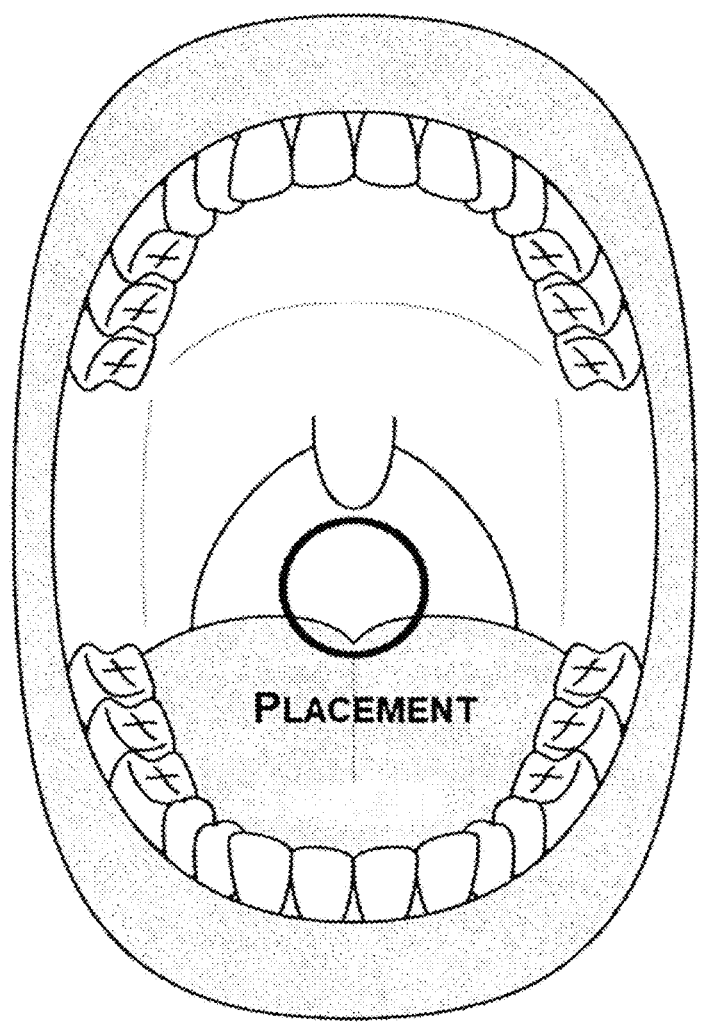

Another aspect of the present discovery pertains to use of a small volume of syrup 1 mL for the delivery of DIPA-1-9 to the oropharyngeal surface. The rapid transit time of a bolus (35 cm/sec) pass the oropharynx hinders any contact time with the nerve endings of the pharynx. Using a medication dissolved in saliva requires constant secretion and swallowing to coat the pharynx, and is not convenient. The placement of the DIPA-1-9 syrup combination, however, as shown in FIG. 1 to FIG. 3 achieves excellent results. The syrup vehicle provides a homogeneous distribution system for DIPA-1-9 at its precise desired site of action with immediate onset of effect. As will be appreciated by one of skill in the art, features and preferred embodiments of one aspect of the discovery will also pertain to other aspects of the discovery.

BRIEF DESCRIPTION OF THE SEVERAL VIEW OF OF THE DRAWINGS

FIG. 1. is a drawing of DIPA-1-9 dissolved in syrup and in its delivery unit. The delivery unit is a plastic vial (4.5 cm length) and designed to hold 2 mL of liquid. The fill volume can range from 0.5 to 1.5 mL and the subject is recommended to use half of the volume in the vial per dose.

FIG. 2. is a drawing of the innervation of the human pharynx, demonstrated by the Sihler's stain. The target for placement of the DIPA-1-9 syrup is shown in the black-outlined circle, at the base of the tongue. The drawing is adapted from Mu and Sanders, "Sensory nerve supply of the human oro- and laryngopharynx: a preliminary study." Anatomical Record 258:480-420, 2000. The nerve endings of the upper oropharynx are primarily from the $9^{th}$ nerve (glossopharyngeus), and the nerve endings for the laryngopharynx from the $10^{th}$ nerve (vagus). The lateral and posterior walls of the oropharynx are innervated by both the $9^{th}$ and $10^{th}$ nerves. Epi=epiglottis, medium black areas=tonsils, and the small black areas are lymph granules. These sensory nerve endings transduce the signals from the pharynx to the brain and coordinate sensory perception and muscular response.

FIG. 3. is a drawing of the human oral cavity and show the target area for placement of the DIPA-1-9 syrup (black outlined circle), at the base of the tongue. The sensory nerve endings for the detection of coolness are abundant in the upper oropharynx and also at the bases of the anterior arches of the pharynx, called the pillars of fauces. The delivery of the DIPA-1-9 syrup to the target site transduces signals of coolness from the pharynx to the brain.

Figure 4:
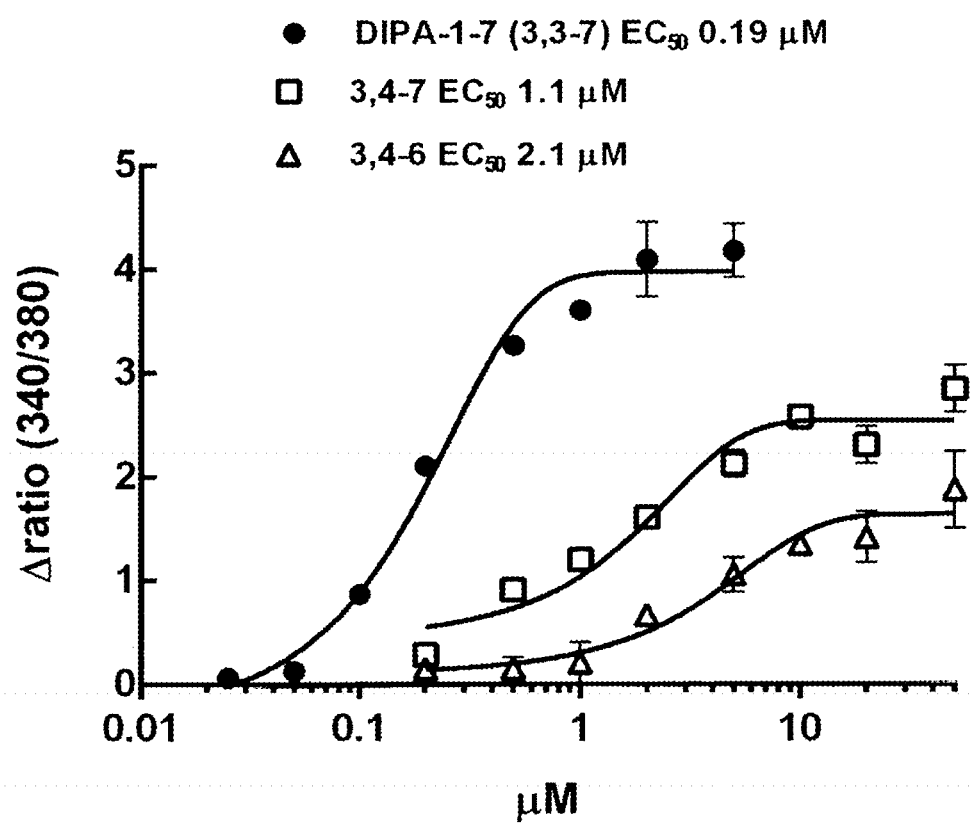

FIG. 4. is a graph of fluorescence response (Δ ratio 340/380) in TRPM8 transfected cells as a function of the logarithm of the concentration of the test compound, expressed in µM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and polyunsaturated fatty acids. Journal Neuroscience 27 (12): 3347-3355, 2007.

Figure 5:
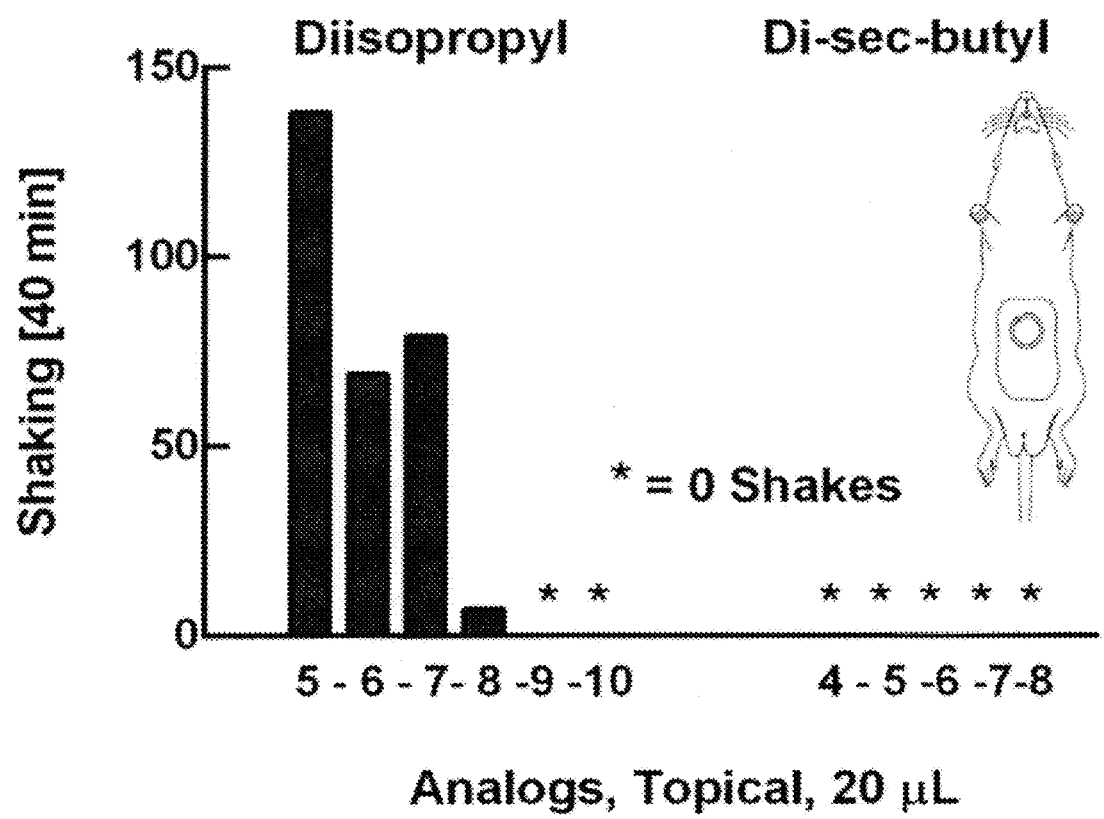

FIG. 5. shows the flux of DIPA-1-7 and DIPA-1-9 through excised hairless mouse skin in vitro. Test chemicals dissolved in a gel were placed in an incubation well for 8 hr and the permeated amount of the chemical measured by a high pressure liquid chromatograph equipped with a refractive detector. These tests were conducted by Prof Choi of Chosun University, Korea. The flux of DIPA-1-7 was ~5× greater than DIPA-1-9. Standard enhancers with polyhydric alcohols, such as a propylene glycol-oleyl alcohol mixture (50:50) or Lauroglycol 90, designed to increase permeation added to the DIPA-1-7 gel decreased the rate of permeation by ~50%, indicating the importance of water solubility for permeation.

Figure 6:
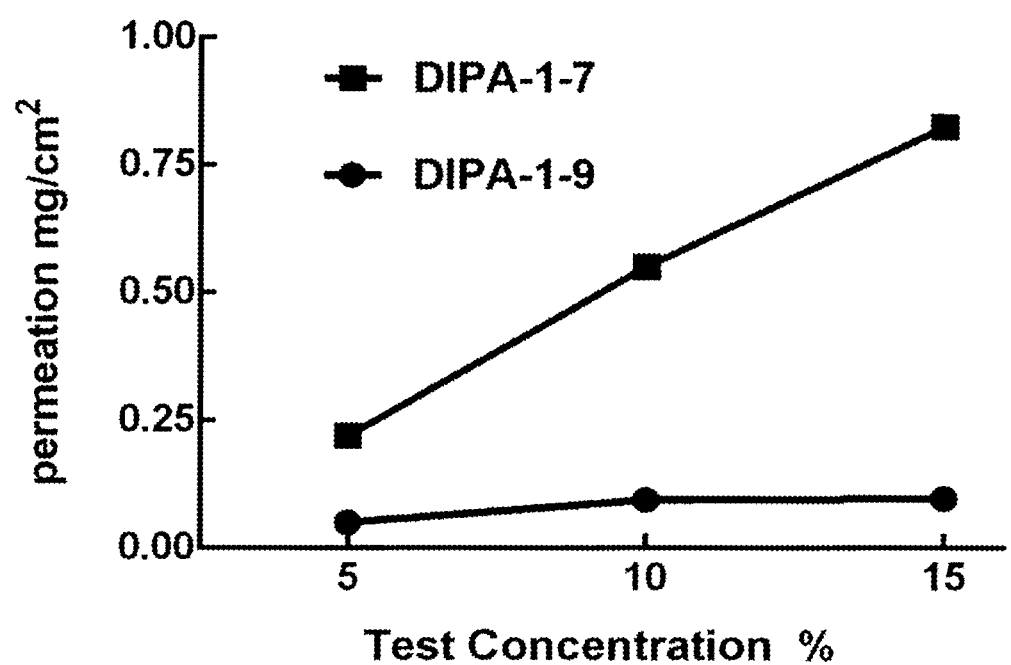

FIG. 6. shows the method for estimating the in vivo transdermal activity of the DIPA-embodiment compounds (without solvent) applied with a micropipette 20 µL to the center of a circle enclosed by cream on abdominal skin of an anesthetized rat. Shaking frequency was counted for 40 min after topical application. It can be seen that the embodiments DIPA-1-5, DIPA-1-6, and DIPA-1-7 evoke robust shaking, indicating transdermal absorption into the bloodstream, but this is not seen with other analogs.

Figure 7:
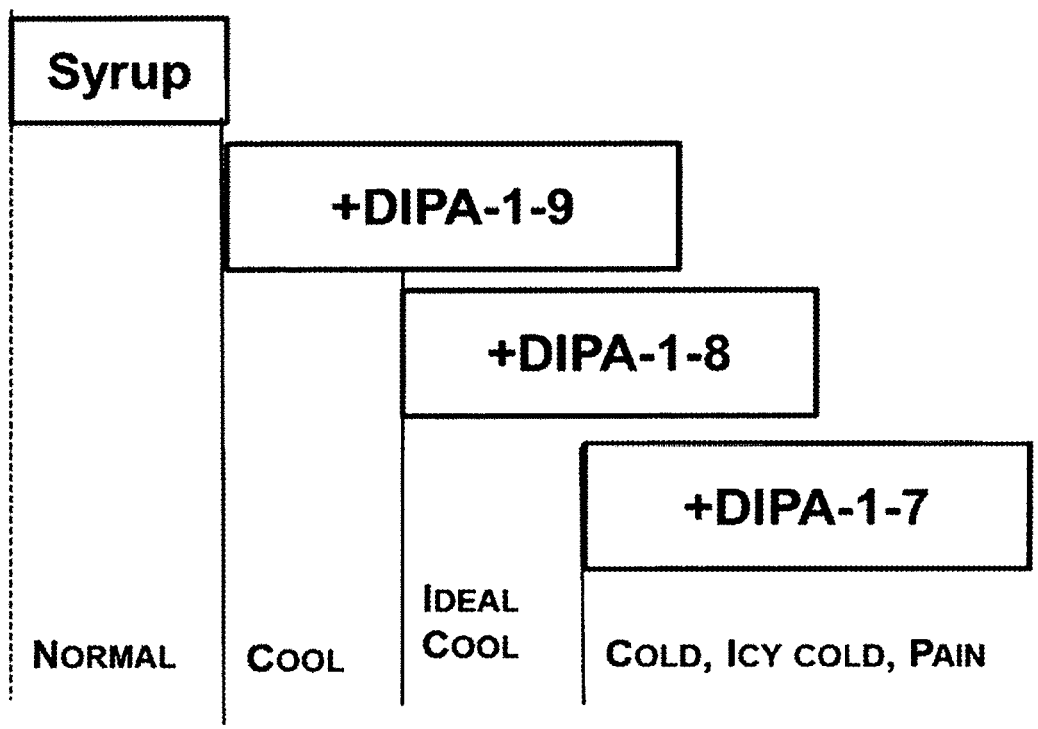

FIG. 7. shows a comparison of the sensory effects of DIPA-1-7, DIPA-1-8, and DIPA-1-9 administered to the base of the tongues of 4 volunteers using a 2 mL vial for delivery. The DIPA compounds was 5 mg/mL in cherry-flavored syrup in a volume of 0.8 mL per dose. The sensory effect were recorded every 5 min for 1 hr.

Figure 8:
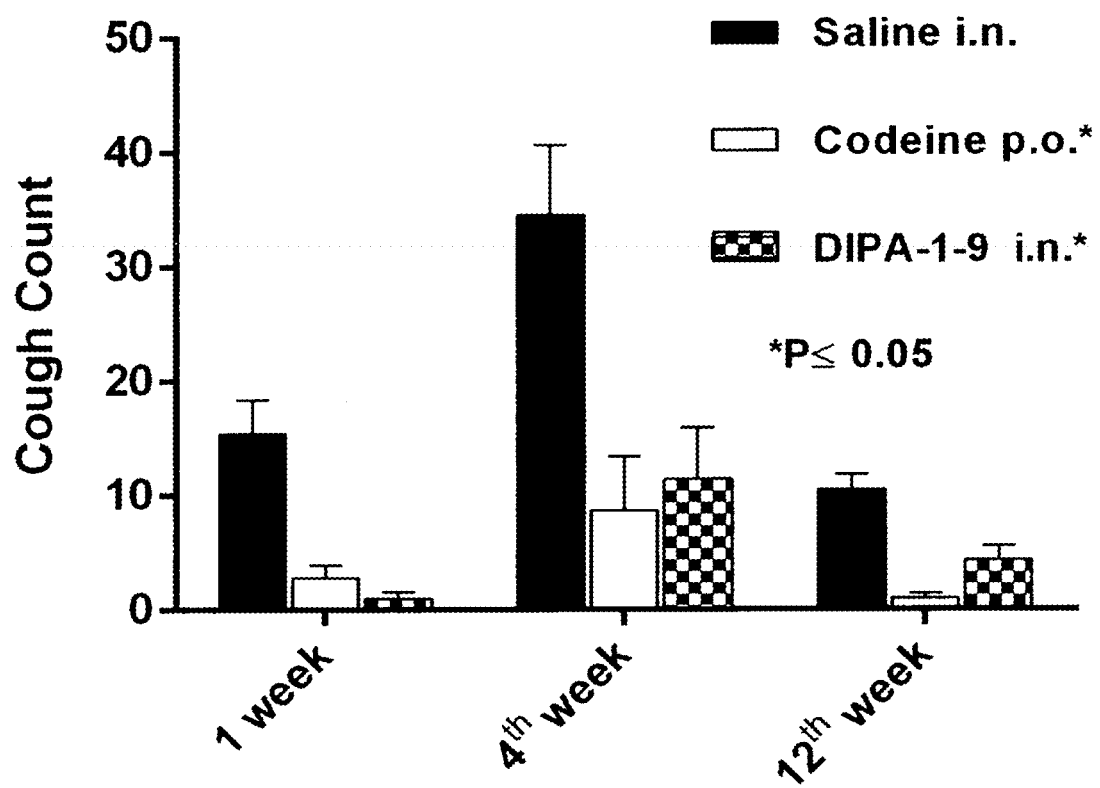

FIG. 8. shows DIPA-1-9 inhibits cough frequency in a mouse model of respiratory tract viral infection. Mice (n=4 to 6 per group) cough more frequently (black bars) after inoculation with respiratory synctial virus (RSV). Codeine administered 1 mg perioral (p.o.) per mouse, or DIPA-1-9 0.5 mg in 25 µL intranasally (i.n.) per mouse, significantly inhibited cough frequency (*P≤0.01 and ≤0.05 for the three time periods of testing, Dunnett's test for multiple comparison). These results in mice show that DIPA-1-9 has potential antinociceptive activity in the upper aerodigestive tract.

DETAILED DESCRIPTION OF THE INVENTION

The present discovery pertains specifically to the selection of one particular active ingredient called 1-Diisopropyl-phosphinoyl-nonane and referred to herein as "DIPA-1-9". Surprisingly and unexpectedly, DIPA-1-9, is able to treat (e.g., selectively suppress) sensory discomfort from the upper aerodigestive tract without the problems of stinging or irritancy, for example, as found with structurally similar compounds. The onset of effect is immediate 1 min) and surprising: there are no other products on the market that match this rapid action. Consequently, DIPA-1-9 is useful, for example, in the treatment of disorders sensory discomfort from the upper aerodigestive tract discomfort including medical conditions of oropharyngeal discomfort, esophageal discomfort, throat irritation, cough, heartburn, dysphagia, dyspnea, dyspepsia, chest pain, and acid reflux discomforts. The present discovery also pertains to pharmaceutical compositions comprising DIPA-1-9, and the use of DIPA-1-9 compositions, for example, in therapy.

As described herein, the Inventor has re-investigated the cooling phosphine oxide compounds with the goal of finding an optimal efficacious and specific candidate to soothe the surfaces of the pharynx and esophagus, which unlike the tongue, do not have a keratinized layer. The goal was to find single agents for use as pharmaceuticals, and not an agent for comestibles or toiletries. Therefore, the logic of the mechanisms of action, target surfaces, screening methods, bioassays, and animal models is for the upper aerodigestive tract, and not the skin.

Surprisingly and unexpectedly, one compound, referred to herein as DIPA-1-9, was found to have an ideal combination of properties for the medical treatment of the surface of the aerodigestive tract. As described in the studies below:

- The diisopropyl substitution on the molecule makes DIPA-1-9 entity more water soluble and facilitates delivery to the surfaces of pharyngeal and esophageal membranes.
- The formulation of DIPA-1-9 in a small volume of syrup (~0.5 mL per dose) allowed precise dosage of DIPA-1-9 to the target nerve endings of the oropharyngeal surface.
- DIPA-1-9 evokes a strong cooling sensation on the throat, but without unpleasant taste or pain. The comparison was against 14 other analogs.
- A precise definition of the cooling action of DIPA-1-9 syrup, analogous to the swallowing of a spoonful of a rich ice cream, such as Haagen-Dazs ice cream, allowed it to be differentiated from other analogs which produced cold discomfort.
- DIPA-1-9's cooling sensations are sufficiently prolonged [15 min] to be of therapeutic benefit in multiple indications. Application to the throat also leaves a residual antinociceptive effect that lasts 3 hr.
- The unusual properties of DIPA-1-9 relative to other analogs could not have been predicted based on its TRPM8 receptor activation potency, but had to be discovered by experiment. There is no direct correlation between the $EC_{50}$ [measurement of TRPM8 potency] and efficacy for activity on the pharyngeal and esophagela epithelia.
- DIPA-1-9 inhibited cough frequency in a respiratory syncytial virus induced model of cough in the mouse.
- When tested in volunteers with upper aerodigestive tract discomfort, a formulation of DIPA-1-9 in a syrup had a rapid onset of action of 1 min and reduced discomfort without adverse effects.
- No current medications of the aerodigestive tract, for example, for cough or for acid indigestion, have such properties of rapid onset and efficacy.

These results, in multiple test systems, show that DIPA-1-9 exhibits unusual selective and specific drug actions. Consequently, DIPA-1-9 is useful, for example, in the treatment of disorders (e.g., diseases) of sensory discomfort from the upper aerodigestive tract.

Abbreviations and Terminology

Upper Aerodigestive Tract. The lumen of the upper aerodigestive tract is the common anatomical conduit for food, liquid, and air into the body, and is part of both the digestive and respiratory systems. This tract is composed of the mouth, pharynx, larynx, and parts of the esophagus. In laymen's terms it includes the organs and tissues of the lips, mouth, tongue, nose, throat, vocal cords, and parts of the esophagus and windpipe. (McGraw-Hill Concise Dictionary of Modern Medicine, 2002). Here, the target for topical delivery of the preferred embodiment, DIPA-1-9 in syrup, is on the rostral edge of the oropharynx. The disorders that promote the use of the preferred embodiment can originate from any parts of the upper aerodigestive tract. The term "upper" aerodigestive tract is used to distinguish it from the "lower" digestive tract which includes the stomach and intestines. Sometimes the sinonasal tract is included in the upper aerodigestive tract descriptor, but food is not present in the sinonasal tract. The primary functions of the aerodigestive tract are to regulate mastication and swallowing of food and breathing, and to operate these two functions without a mixup.

DIPA compounds DIPA is the abbreviation for 1-[Diisopropyl-phosphinoyl]-alkane. The third alkyl group in the molecule may be described by a number: hence, 4, 5, 6, 7, 8, 9, and 10 correspond to the butyl, pentyl, hexyl, heptyl, octyl, nonyl, and decanyl side chain, respectively. These alkanes are linear or "normal [n]" in configuration, with the phosphinoyl group attached to the primary, or "1-" position, of the carbon chain in the third sidechain. These compounds are also known as trialkylphosphine oxides or as 1-dialkylphosphorylalkanes.

TRP channels The transient receptor potential (TRP) family of cation channels are peripheral detectors of nociceptive and painful stimuli. Many of these receptors are located on the nerve membranes of sensory neurons and respond to chemical irritants and changes in local temperature by activating nerve action potentials which are the signals to be perceived and acted upon by the brain. The TRP receptors are the transducers of sensory information, and it is this transduction and effector system that regulates and protects the organism from external irritants.

Receptive field of a sensory neuron is the region in space in which a stimulus will modify the firing of the neuron. The receptive field is spatially determined by the distribution of the nerve endings of the neuron. For the epithelium, the nerve endings are interdigitated with the cell layers at the basal layer of the epithelium. A receptive field, even though smaller than a $mm^2$, when activated by the appropriate stimulus, e.g. nociceptive or pruritic, can totally dominate the attention of the brain and mind. Witness what happens when a sharp pin or sting comes into contact with skin or when a dog is pre-occupied with a flea bite.

Cold Discomfort This term is used to describe three types of sensations—"icy cold", coldness in the chest, and systemic coldness. Icy cold can be felt in the throat and esophagus and can be acutely painful. Coldness in the chest is felt behind the sternum and is equally uncomfortable. Systemic coldness is equivalent to chills, and is felt first around the eyes, then the skin of the shoulder blades and ankle. Cold discomfort limits selection of the active ingredient for localized action on the oropharynx and upper esophagus. The ideal agent must have a circumscribed site of action, and the intensity of the sensation should not cause "icy cold", coldness in the chest, or systemic chills. As shown in the discovery, DIPA-1-9 is selected as an ideal agent because its water solubility and pharmacokinetic properties permit access to receptors in the basal layer of the stratified pharyngeal epithelia, but not to penetrate too deeply into the systemic circulation, or to over-activate the cold receptors in the thinner epithelial layers of the larynx and esophagus. Thus, DIPA-1-9 will produce refreshing cool but not cold discomfort.

Syrup. A syrup (medicated) is a concentrated or nearly saturated solution of sucrose in water. A simple syrup contains only sucrose and purified water (e.g. Syrup USP). Syrups containing pleasantly flavored substances are known as flavoring syrups (e.g. Cherry Syrup, Acacia Syrup, etc.). Syrup, USP contains 850 gm sucrose and 450 ml of water in each liter of syrup. The syrup resists mold or bacterial contamination and growth. The syrups used in the studies here were obtained from Humco Compounding, Austin, Tex. and were Simple Syrup (85% w/v of sucrose in purified water, with citric acid and 0.1% methylparaben as a preservative) or as cherry flavored syrup. In this application, the syrup is not utilized for its sweetness or as a vehicle for transporting a medication into the gastrointestinal tract. Sweetness is detected in, the front ⅓ of the tongue. The delivery site here is the back of the tongue. Instead, the active water soluble ingredient DIPA-1-9 is miscible with the syrup. The volume of syrup per dose is small, less than 1 mL and preferably 0.5 mL, and administered onto the base of the tongue, and designed to coat the oropharyngeal walls. In standard cough syrups, the recommended single dosage volume is two teaspoons (~10 mL) for adults and one teaspoon (~5 mL) for children, administered three to four times a day. Such large volumes are not relevant to this application as a large volume will not work for a cooling agent designed to be focally delivered onto nerve endings of the pharyngeal wall. In liquid volumes ≥1 mL, the cooling agent solute will move too quickly past the pharyngeal receptors to have the desired pharmacological effect.

Teaspoon. A unit of measure used in cookery. According to the US Code of Federal Regulations § 101.9, a teaspoon is equal to 5 milliliters. This liquid volume may vary slightly among countries such as USA, Australia, and the United Kingdom.

DIPA and DAPA Compounds
DPAP and DIPA Compounds

The discovery relates to a particular compound within the series of compounds known as phosphine oxides (which have the following general formula), and more particularly, an example of the group known as di-alkyl-phosphinoyl-alkanes (herein referred to as "DAPA compounds") (wherein each of $R_1$, $R_2$, and $R_3$ is an alkyl group).

(O═)P $R_1R_2R_3$

And more specifically, to one particular 1-diisopropyl-phosphinoyl-alkane (DIPA), 1-Diisopropyl-phosphinoyl-nonane, referred to herein as "DIPA-1-9".

TABLE 1

Chemical structure of DIPA-1-9

| Code | Chemical Name | Formula/ Weight | Chemical Structure |
|---|---|---|---|
| DIPA-1-9 | 1-Diisopropyl-phosphinoyl-nonane | $C_{15}H_{33}OP$ 260.40 | 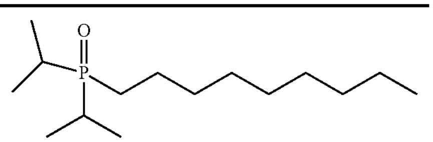 |

DIPA-1-9 is a liquid at room temperature, with a density of ~0.92 g/cm³ and a boiling point of 112-120° C. Note that DIPA-1-9 is achiral and does not have enantiomers.

By comparison to related DAPA compounds, the Inventor has identified DIPA-1-9 as an exceptional agent for the treatment of sensory discomfort arising from the epithelia, including mucous membranes, of the upper aerodigestive tract, for example, the oropharyngeal (including, e.g., the oropharynx and hypopharynx) and upper esophageal surfaces. The applicant has reported on the efficacy of DIPA-1-9 for the mucous membranes of the nasal cavity and for the transitional epithelium of the ocular surface (U.S. Pat. Nos. 9,642,868 and 9,895,382). This is the first detailed report of the activities of DIPA-1-9 on the aerodigestive tract.

As described herein, DIPA-1-9 is selective and specific and ideal for evoking localized cooling in the oropharynx without discomfort. This refreshing sensation of cool/cold is the desired sensory quality for relieving oropharyngeal/esophageal discomfort. By topical administration the DIPA-1-9 sensation is localized. In an animal model, DIPA-1-9 inhibited capsaicin induced coughing. DIPA-1-9 is not an irritant in the oral cavity of human volunteers or when it was put into the throat where it exerted the desired antinociceptive effect. The receptive element on neuronal membranes for DIPA-1-9 was further identified as TRPM8, an ion channel receptor.

Unlike related analogs, DIPA-1-9 did not produce stinging, or "icy cold" pain, even when the dose was increased to 12 mg per unit. By choosing syrup as a delivery vehicle, the activity of DIPA-1-9 was confined to the throat and upper esophagus, and there was no systemic cooling. The syrup was used as a vehicle and not because it imparted sweetness (volume and location of delivery does not result in sweetness) and because, as a liquid, it allowed homogeneous delivery to the pharyngeal surface. Individuals with throat discomfort preferred DIPA-1-9 because of the rapid onset and the pleasant cool sensation. The "icy cold" seen with other DAPA compounds (DIPA-1-6, DIPA-1-7, DAPA-2-6, and DAPA-2-7) was considered to be too cold, even though these compounds had an equivalent fast onset or were longer-acting. The activity of other DAPA compounds (DIPA-1-6, DIPA-1-7, DAPA-2-6, and DAPA-2-7) spreads behind the sternum, into the chest, most likely because of activation of sensory elements in the oesophageal lining. This central sternum cooling is perceived by the subject as unpleasant. The duration of action of DIPA-1-9 was sufficient to be therapeutically useful.

Chemical Synthesis

DAPA compounds were prepared by the following general method: 100 mL (23.7 g, ~200 mmol) of sec-butylmagnesium chloride or bromide (isopropylmagnesium chloride or bromide) (obtained from Acros, as a 25% solution in tetrahydrofuran (THF)) was placed under nitrogen in a 500 mL flask (with a stir bar). Diethylphosphite solution in THF (from Aldrich, D99234; 8.25 g, 60.6 mmol in 50 mL) was added drop-wise. After approximately 30 min, the reaction mixture warmed up to boiling. The reaction mixture was stirred for an extra 30 min, followed by a drop-wise addition of the appropriate n-alkyl iodide solution in THF (from TCI; 60 mmol in 20 mL). In the case of DIPA-1-9, the n-alkyl halide was 1-iodononane. The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under high vacuum. The final products, verified by mass as determined by mass spectrometry, were clear liquids that were colourless or slightly pale yellow.

The compounds prepared by these methods are shown in Table 2.

TABLE 2

Chemicals prepared and tested.

| Code | Chemical Name | Chemical Structure |
|---|---|---|
| DIPA-1-5 | 1-Di(isopropyl)-phosphinoyl-pentane | 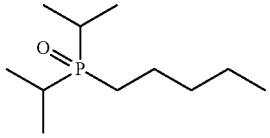 |
| DIPA-1-6 | 1-Di(isopropyl)-phosphinoyl-hexane | 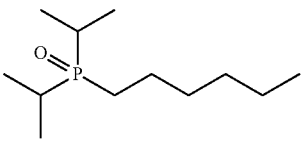 |
| DIPA-1-7 | 1-Di(isopropyl)-phosphinoyl-heptane | 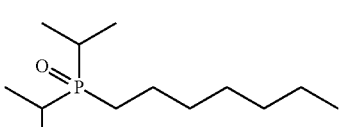 |
| DIPA-1-8 | 1-Di(isopropyl)-phosphinoyl-octane | 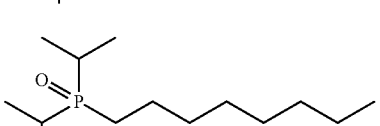 |
| DIPA-1-9 | 1-Di(isopropyl)-phosphinoyl-nonane | 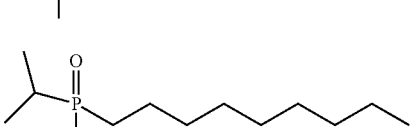 |
| DAPA-2-4 | 1-Di(sec-butyl)-phosphinoyl-butane | 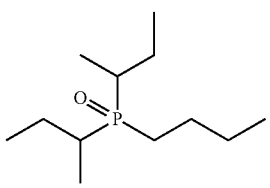 |
| DAPA-2-6 | 1-Di(sec-butyl)-phosphinoyl-hexane | 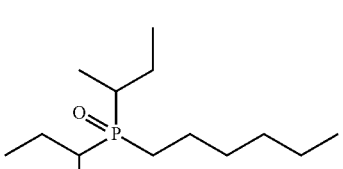 |
| DAPA-2-7 | 1-Di(sec-butyl)-phosphinoyl-heptane | 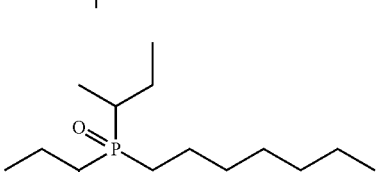 |
| DAPA-2-8 | 1-Di(sec-butyl)-phosphinoyl-octane | 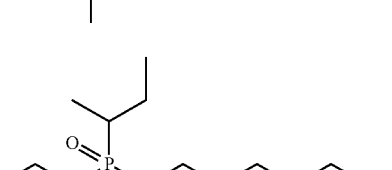 |

TABLE 2-continued

Chemicals prepared and tested.

| Code | Chemical Name | Chemical Structure |
|---|---|---|
| 3,4-6 | 1-(Isopropyl-sec-butyl)-phosphinoyl-hexane | 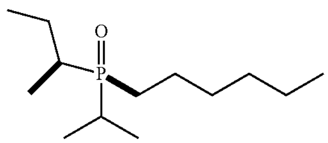 |
| 3,4-7 | 1-(Isopropyl-sec-butyl)-phosphinoyl-heptane | 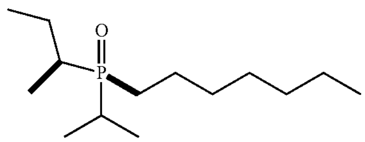 [SMILES: CCCCCCC[P@@](=O)(C(C)C)[C@@H](C)CC] |
| DAPA-3-1 | 1-di(iso-butyl)phosphinoyl-pentane | 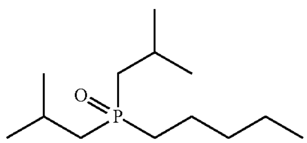 |
| DAPA-3-2 | 1-Di(sec-butyl)phosphinoyl-3-methyl-butane | 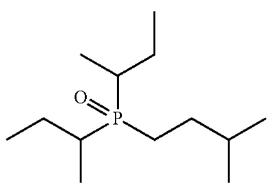 |

Compositions The 3,4-X series are "mixed" isopropyl-sec-butyl compounds (see below). These were synthesized by Dr. Jae Kyun Lim of Dong Wha Pharmaceuticals, using the method described below.

Briefly, as illustrated in the following scheme, triethyl phosphite (A) was reacted with sec-butyl magnesium bromide (B) and then hydrolysed with dilute hydrochloric acid to give the mono-alkyl compound (C). The product (C) was then reacted isopropyl magnesium bromide (D) to give the di-alkyl compound (E), which was then reacted with a suitable alkyl iodide (F) to give the target trialkyl phosphine (G).

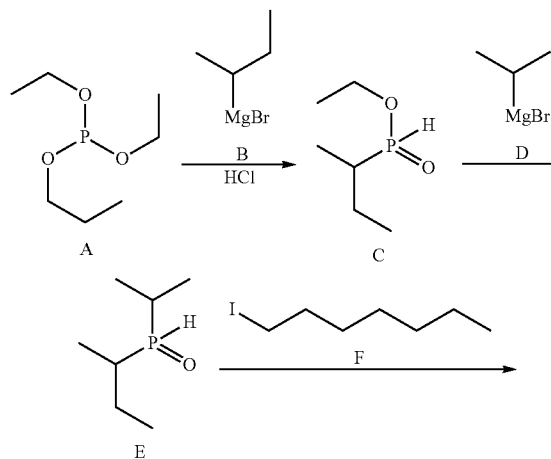

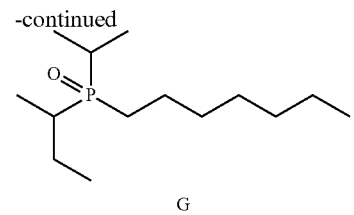

-continued

G

The DIPA compounds are colorless liquids with a density less than water. These structures differ from those described by Rowsell and Spring U.S. Pat. No. 4,070,496 because '496 structures have their "head" (phosphine oxide group) covered by larger, more lipophilic groups. The applicant noted that '496 did not include the di-isopropyl analogs. The applicant synthesized these analogs (which are achiral, by contrast to the structures of '496 which are >95% chiral). The applicant found that, by minimizing the two alkyl side chains to di-isopropyl, the "head" of the prototypical molecule now is more polar (hydrophilic) and more miscible in the polar environment of water. This increased water-solubility is striking (Table 3). The water solubility of the DIPA if at least 10× greater than the di-sec-butyl or the mixed isopropyl-sec-butyl analogs. The DIPA analogs are now mobile in the extracellular fluids and permeate between cells to access nerve endings in the stratum basale.

TABLE 3

Water solubility (mg/ml) of 1-dialkylphosphorylalkanes ($R_1R_2R_3P = O$).

| No. Carbons | 13 | | 14 | | 15 | | 16 | |
|---|---|---|---|---|---|---|---|---|
| $R_1, R_2$ | $R_3$ | | $R_3$ | | $R_3$ | | $R_3$ | |
| di-sec-butyl- | pentane | 22 | hexane | 8 | heptane | <3 | octane | <3 |
| isopropyl-sec-butyl- | hexane | 25 | heptane | 20 | octane | <3 | nonane | <3 |
| di-isopropyl- | heptane | >300 | octane | >300 | nonane | >300 | decane | <3 |

The discovery also relates to a composition (e.g., a pharmaceutical composition) comprising DIPA-1-9, and a pharmaceutically acceptable carrier, diluent, or excipient. The discovery also relates to a method of preparing a composition (e.g., a pharmaceutical composition) comprising mixing DIPA-1-9, and a pharmaceutically acceptable carrier, diluent, or excipient.

In one embodiment, the composition comprises DIPA-1-9 at a concentration of 0.05-2.0% wt/vol. In one embodiment, the composition is a liquid composition, and comprises DIPA-1-9 at a concentration of 0.5-20 mg/mL In one embodiment, the composition is a liquid composition, and comprises DIPA-1-9 at a concentration of 3 to 12 mg/mL. In one embodiment, the composition is a syrup and comprises DIPA-1-9 at a concentration of 1-20 mg/mL.

The composition may be provided with suitable packaging and/or in a suitable container. For example, the composition may be in the form of unit oral dosage unit, for example, a plastic vial, a lozenge, jelly cup, or film strip comprising DIPA-1-9. Alternatively, it can be delivered as a spray.

One aspect of the present discovery pertains to DIPA-1-9 for use in a method of treatment (e.g., targeted treatment) of certain disorders (e.g., a diseases), as described herein. In one embodiment, the medicament comprises DIPA-1-9. In one embodiment, the medicament comprises DIPA-1-9 formulated in a syrup and applied with a plastic vial. Another aspect of the present discovery comprises administering to a patient in need of treatment a therapeutically effective amount of DIPA-1-9, preferably in the form of a pharmaceutical composition.

Sensory Discomfort and Treatment Objectives

In one embodiment (e.g., of use in methods of therapy, of use in the manufacture of medicaments, of methods of treatment), the treatment is treatment (e.g., selective treatment) of: sensory discomfort from the surfaces of the pharynx and larynx such as; upper aerodigestive tract discomfort; oropharyngeal discomfort; esophageal discomfort; throat irritation; cough; heartburn; chest pain; anogenital discomfort; or inflammation of pharyngeal and esophageal tissues: In an another aspect treatment, the DIPA-1-9 is used to stimulate coolness receptors and produce signals that will prevent dysphagia and dyspnea, and alleviate the condition known as sleep apnea. In another aspect of treatment, the DIPA-1-9 is used to facilitate the expectoration of mucus from the airways.

The term "sensory discomfort", as used herein, relates to irritation, pain, itch, or other form of dysesthesia arising from the lumen of the upper aerodigestive tract. The term "dysesthesia" as used herein relates to abnormal sensation, and includes, in addition to irritation, itch, and pain, sensations such as burning, dryness, wetness, pins-and-needles, and feeling the presence of a foreign body.

In one of the embodiments, the target tissue for DIPA-1-9 is located on an oropharyngeal surface, a hypopharyngeal surface, or a pharyngeal surface. In one of the embodiments, the sensory discomfort from the target tissue is caused by dysphagia, by mechanical compression and dyspnea, by mucus accumulation, by reflux of stomach contents (e.g., laryngopharyngeal reflux), by hiccups, by pharyngitis, by tonsillitis, by mucositis, by an allergy, by cough, or by hypersensitivity of the pharyngeal surface to an irritant.

In one of the embodiments, the target tissue for DIPA-1-9 is located on an esophageal surface and the sensory discomfort located on an esophageal surface is caused by reflux of stomach contents (e.g., gastroesophageal reflux) or by esophagitis. In one embodiment, the upper aerodigestive tract discomfort is caused by inflammatory exudates in the airways or the pharynx (e.g., associated with asthma, an obstructive pulmonary disorder, etc.). In one embodiment, the upper aerodigestive tract discomfort is associated with labored breathing, dyspnea, snoring, or sleep apnea. In one embodiment, the treatment is treatment of oropharyngeal discomfort. In one embodiment, the oropharyngeal discomfort is associated with reflux of stomach contents. In one embodiment, the oropharyngeal discomfort is associated with laryngopharyngeal reflux. In one embodiment, the treatment is treatment of esophageal discomfort. In one embodiment, the esophageal discomfort is associated with reflux of stomach contents. In one embodiment, the esophageal discomfort is associated with gastroesophageal reflux. In one embodiment, the treatment is of throat irritation. In one embodiment, the treatment is treatment of cough or the urge to cough. In one embodiment, the treatment is treatment of heartburn. In one embodiment, the treatment is treatment of chest pain.

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Inclusive of such treatments are reduction of sensitivity, of hypersensitization, and desensitization phenomena. Treatment as a prophylactic measure (i.e., prophylaxis) is also included. For example, use with patients who have not yet developed the disorder, but who are at risk of developing the disorder, is encompassed by the term "treatment."

The term "selective" in pharmacological terminology pertains to a molecule that, among a group of structurally related congeners, exhibits unusual qualitative properties that distinguishes it from the other analogs. For example, DIPA1-9 does not have a strong metallic taste, but this taste is present in DIPA-1-7 and DIPA-1-8 and other analogs. Thus, DIPA-1-9 is more selective in its pharmacological actions.

Another aspect of the selective properties of DIPA-1-9 is the low degree of "cold discomfort" compared to the related analogs. DIPA-1-9 can act on surfaces without problems of stinging, irritancy, and pain in the throat or excessive cold behind the sternum.

The "specificity" of the DIPA-1-9 action relates to its efficacy for producing the desired Haagen-Dazs cooling effect. Although all the active analogs are active on the TRPM8 receptor, only DIPA-1-9 fully produces the desired cooling sensation. Hence, it is more specific for the desired drug action.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

DIPA-1-9 in syrup may be used as a diagnostic agent for the differential diagnosis) of chest pain. Currently, a simple diagnostic tool is not yet known. A DIPA-1-9 syrup can be administered orally, e.g., as an aliquot placed on the base of the tongue. If the pain is of esophageal origin, the pain should be relieved. But, if the pain is cardiac pain, then the DIPA-1-9 syrup will not be effective.

Routes of Administration

The pharmaceutical composition comprising DIPA-1-9 may suitably be administered to a subject topically, for example, as described herein. The term "topical application", as used herein, refers to delivery onto the lumenal surfaces of the pharyngx and esophagus.

The subject/patient may a mammal, for example, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. In one preferred embodiment, the subject/patient is a human.

Formulations for Delivery

The preferred formulation of DIPA-1-9 is to dissolve it in syrup. Other ingredients that may be included are fillers, buffers, preservatives, anti-oxidants, lubricants, stabilisers, masking agents, colouring agents, and flavoring agents. The formulation may further comprise other active pharmacological agents. If formulated as discrete units (e.g., vials, pre-wrapped units), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005. The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers).

Dosage

It will be appreciated by one of skill in the art that appropriate dosages of DIPA-1-9, and compositions comprising DIPA-1-9, can vary from patient to patient. Determining the optimal dosage will generally involve the balancing of the level of therapeutic benefit against any risk or deleterious side effects. The selected dosage level will depend on a variety of factors including, but not limited to, the activity of DIPA-1-9, the route of administration, the time of administration, the duration of the treatment, other drugs, compounds, and/or materials used in combination, the severity of the disorder, and the species, sex, age, weight, condition, general health, and prior medical history of the patient. The amount of DIPA-1-9 and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, preferably on an "as-need" or pro re nata basis throughout the course of treatment. Methods of determining the most effective means and dosage of administration are well known to those of skill in the art and will vary with the formulation used for therapy, the purpose of the therapy, the target receptors being treated, and the subject being treated. Single or multiple administrations can be carried out with the dose level and pattern being selected by the patient, treating physician, veterinarian, or clinician.

Upper Aerodigestive Tract and its Disorders

Air enters the nasal cavity and goes to the trachea. Food, air, and liquids enter the mouth, goes past the pharynx, and into the esophagus and stomach. The tube that forms these passages is the upper aerodigestive tract. In this application, it is the oropharynx, hypopharynx (laryngopharynx), and upper third of the eosophagus that are selected as part of DIPA-1-9 syrup targets.

The oral cavity contains specialized structures such as teeth, gums, tongue, and salivary glands that are designed to masticate, taste, lubricate, and propel the food bolus into the pharynx. This is a complicated muscular reflex activity that requires the coordination 6 cranial nerves and 25 muscle groups. Heat sensation is not a high ranking protective reflex in the oral cavity as the mouth can tolerate hot liquids which are painful when put on the skin. Cooling liquids, on the other hand, are important in the regulation of thirst. Eccles et al. [Cold pleasure. Why we like ice drinks, ice-lollies and ice cream. Appetite, 71, 357-60, 2013] recently reviewed this concept on the relationships of cooling liquids, ice creams, positive reinforcement, and the suppression of thirst. Sensory nerves closely monitor temperatures at the junction of the oral cavity and pharynx. When the external ambient temperature is high, drinking cooling liquids is instantly pleasurable and relieves thirst, dryness, and discomfort.

The pharynx is a cone-shaped passageway leading from the nasal and oral cavities to the larynx and esophagus. The pharynx is part of the throat, an inexact term describing the region of the body around the neck and voice-box. The pharynx is divided into three regions: naso-, oro- and laryngo-. The nasopharynx, also called the rhinopharynx, lies behind the choanae of the nasal cavity and above the level of the soft palate. The oropharynx reaches from the soft palate (velopharynx) to the level of the hyoid bone. The laryngopharynx (also called hypopharynx) reaches from the hyoid bone to the lower border of the cricoid cartilage. The pharyngeal and esophageal surfaces are lined with stratified epithelium. By contrast, the respiratory epithelia of the nasopharynx, larynx and trachea are a single layer of cells.

The oropharynx may be further divided into an upper and lower region, the mid-point being what is called the lower retropalatal oropharynx (LRO) as shown, for example, in the magnetic resonance imaging studies of Daniel et al. ["Pharyngeal dimensions in men and women", *Clinics (SaoPaulo)*

62, 5-10, 2007]. The pharynx is a trapezoid inverted funnel-shaped tube and the LRO is the region with smallest cross-section, an area of about 1 cm$^2$, which is equivalent to 20% of US quarter coin of 25% of a Euro coin. The pharyngeal surface at the base of the tongue and the pharyngeal wall around the LRO, with a total area of about 3 to 5 cm$^2$, is one part of the desired target for drug delivery for the methods described herein, the second part being the upper esophageal surface.

The traffic that passes through the lumen of the oropharynx every day is astounding. On an average day, an adult breathes 12,000 L of air, drinks 2 L of fluids, secretes 1 L of saliva, and eats 2 kg of food. These activities are constant, with about 15 breaths and 1 swallowing movement per min during the waking hours. For the organism to survive, the traffic flow must be co-ordinated so that food and liquids go down the esophagus and not into the airways, and air gets directed into the airways.

The brain co-ordinates pharyngeal traffic via striated and smooth muscle effectors, For solids, the food is masticated, mixed and lubricated with saliva, and the bolus is then rapidly pushed down to the esophagus. The oropharyngeal phase of swallowing occurs in the blink of an eye, in millisec, as the bolus transits down the pharynx at about 35 cm/sec. The sensory signals that govern this process in the mouth and rostral tongue come from afferents of the trigeminal nerve ($5^{th}$) and hypoglossal nerve (8th). The afferent signals from the oropharynx and posterior surface of the tongue come mainly via glossopharyngeal nerve ($9^{th}$). Signals from the laryngopharynx (also called the hypopharynx) are mainly via the vagus nerve ($10^{th}$). Swallowing and coughing are reflexes designed to direct traffic load to their correct destinations.

The neuronal receptive fields of the epithelia of the upper digestive tract (pharynx and esophagus), sub-served by the $9^{th}$ and $10^{th}$ cranial nerves, are the targets of DIPA-1-9 and shown in FIG. 2. The pharyngeal surface cells have a high turnover rate (on the order of several days) and are sensitive to injury. For example, when there is disorganized traffic of solids or liquids in the pharynx, or when acid and pepsin, or exudates from the lungs, accumulate, the aerodigestive tract will activate the cranial nerves and convey signals of irritation, itch, pain, and the urge to cough. The characteristic manifestations of pharyngeal disorders are globus (the feeling of a lump in the throat), difficulties in swallowing (dysphagia), difficulty in breathing (dyspnea), hoarseness, pain, itch, cough, and redness and swelling of the pharyngeal mucosa. Impairment of airflow by malfunction of the pharynx is associated with acute anxiety and a sense of impending doom.

FIG. 2. is a drawing of the innervation of the human pharynx, demonstrated by the Sihler's stain. The target for placement of the DIPA-1-9 syrup is shown in the black-outlined circle, at the base of the tongue. The drawing is adapted from Mu and Sanders, "Sensory nerve supply of the human oro- and laryngopharynx: a preliminary study." Anatomical Record 258:480-420, 2000. The nerve endings of the upper oropharynx are primarily from the $9^{th}$ nerve (glossopharyngeus), and the nerve endings for the laryngopharynx from the $10^{th}$ nerve (vagus). The lateral and posterior walls of the oropharynx are innervated by both the $9^{th}$ and $10^{th}$ nerves. Epi=epiglottis, medium black areas=tonsils, and the small black areas are lymph granules. These sensory nerve endings transduce the signals from the pharynx to the brain and coordinate sensory perception and muscular response.

The pharynx has strong, constrictor muscles, arranged as a vice and designed to grab the oropharyngeal contents and push the bolus into the esophagus. The anatomy is like the first baseman glove in baseball. There are two important valves in this system: the epiglottis which closes during swallowing, and the upper oesophageal sphincter (UES, or cricopharyngeus muscle) which relaxes to allow the contents to enter the esophagus, then shuts to prevent reflux. Pharyngeal contractions flush and empty the lumen of debris, and by creating negative pressure helps suck contents from the nasal cavity and nasopharynx. Well-toned pharyngeal muscles are important for maintaining patency of the airways, allowing smooth airflow and dysfunction will cause dysphagia, dyspnea, snoring, and sleep apnea.

Examples of upper aerodigestive disorders in which a topical DIPA-1-9 syrup exerting an ideal cool sensation may have utility are:

Pharyngitis:

An inflammation of the pharyngeal lining which is most commonly caused by viral and bacterial agents. A closely related condition is tonsilitis [Bathala, S. and Eccles, R. A review on the mechanism of sore throat in tonsillitis. Journal of Laryngology and Otology, 127: 227-32, 2013]. Chemical pollutants, such as cigarette smoke, can also directly irritate and damage the mucosa. The principal symptoms of pharyngitis and tonsillitis are irritation, itch, and pain or a "sore throat". Prolonged pharyngeal irritation can also lead to a chronic hypersensitivity syndrome manifested by persistent cough (called chronic cough when it is present for more than 8 weeks). The DIPA-1-9 formulation described herein will relieve the discomfort of pharyngitis and cough.

Dysphagia (Swallowing Dysfunction):

Old people, stroke victims, individuals with Parkinson's disease or head and neck cancer have difficulty in swallowing. Oropharyngeal dysphagia is a term applied to the condition where the bolus of food is not properly and efficiently transferred from the pharynx to the esophagus. When particles enter the airways, the result is aspiration pneumonia, a major economic burden in the care of such victims. It has been shown that sensory stimulants such as black pepper, capsaicin-like substances (the active ingredients of chili pepper) administered with a nebulizer, and menthol solutions administered by a nasal tube, shorten the latency for a swallowing reflex in the elderly and thus may be employed to reduce the risks of aspiration pneumonia [Ebihara et al., Sensory stimulation to improve swallowing reflex and prevent aspiration pneumonia in elderly dysphagic people", *J. Pharmacol. Sci.*, 115, 99-104, 2011]. A related condition is called aspiration pneumonitis, when the substances entering the airways come from the esophagus and not the oral cavity.

Post-Nasal Drip:

A condition where increased secretions enter the orpharynx from the mucosa of the nasal cavities and nasopharynx. These secretions may contain inflammatory exudates and may arise from infections or allergy of nasal membranes (for example, allergic rhinitis, and rhinosinusitis). The increased secretions cause throat discomfort, pain, itch, the urge to cough, and a sense of impaired airflow.

Acid Reflux Disease:

This condition consists of symptoms in the upper abdomen, such as fullness, discomfort, early satiation, bloating, heartburn, belching, nausea, vomiting, or pain. Disorders of the upper digestive tract are further sub-divided into "organic" and "functional dyspepsia". Organic dyspepsias (OD) are caused, for example, by peptic ulcer, gastroesophageal reflux disease (GERD), Barrett's esophagus, gastric or esophageal cancer, pancreatic or biliary disorders, intolerance to food or drugs, and infections or systemic diseases. Functional dyspepsias (FD), including NERD, are more complex because objective evidence of pathology is not easily identified, but the symptoms are similar to OD. Management of these conditions includes acid-suppressive drugs, antibiotics to eradicate *H. pylori*, prokinetic agents, fundus-relaxing drugs, antidepressants, and psychological interventions.

Laryngopharyngeal Reflux Disease (LPR) and Esophageal Reflux Disease:

In LPR, stomach acid and pepsin are regurgitated onto the laryngopharyngeal surfaces and causes tissue injury. Normally, proper deglutition and a constricted upper oesophageal sphincter (UES), prevent regurgitation, but when this system is impaired, the acid and pepsin enters the pharyngeal surfaces and can even enter the Eustachian tubes and the nasal sinuses. The result is a syndrome of hoarseness, pain, laryngoedema, and persistent throat clearing. Examination of the larynx shows red and swollen mucosae about the voicebox. A agent that reduces discomfort is likely to be useful in the treatment for LPR. Currently, the primary method of treatment is to reduce acid secretion from the stomach, for example, with the use of proton-pump inhibitors; however, there are no methods to treat the discomfort in the throat. An agent such as DIPA-1-9, formulated for delivery in a syrup offers a novel strategy for therapy of reflux disease.

Dyspepsia and Epigastric Discomfort in the Upper Digestive Tract:

The predominant symptoms of acid reflux disorders and dyspepsia [Oustamanolakis et al., Dyspepsia: Organic vs functional. J. Clin. Gastroenterol., 46, 175-190, 2012] are "heartburn" and non-cardiac chest pains. The pain and discomfort of heartburn is primarily of esophageal origin. Non-cardiac chest pain is pain of esophageal origin and not caused by cardiac dysfunction. Some of the symptoms of heartburn include a burning feeling in the chest just behind the breastbone that occurs after eating and lasts a few min to several hours. The substernal burning sensations tend to radiate up into the neck, come in waves, and are felt more as burning than as pain. Heartburn may also be described as chest pain and is exaggerated by assuming positions which promote gastroesophageal regurgitation, such as bending over or lying on one's back. Heartburn is felt in the midline and not on the lateral sides of the chest. Heartburn may also sometimes be associated with hyperthermia. Other sensations include burning on or at the back of the throat with sour, acidic or salty-tasting fluids in the mouth and throat; difficulty in swallowing and feelings of food "sticking" in the middle of the chest or throat. Heartburn and acid reflux diseases may cause chronic cough, sore throat, or chronic hoarseness.

Excess reflux of acidity and digestive enzymes such as pepsin into the esophagus and pharynx give rise to the discomfort seen in heartburn, GERD, laryngopharyngeal reflux disease (LPR), non-erosive reflux disease (NERD), non-cardiac chest pain (NCCP), and functional dyspepsias.

A provocation test, using 0.1 N HCl perfusion of the esophagus alternating with saline perfusion (Bernstein test), can be used to elicit heartburn in susceptible individuals and to prove esophageal origin of the symptoms, e.g., to determine if chest pain is caused by acid reflux. For this test, a thin tube is passed through one nostril, down the back of the throat, and positioned into the middle of the esophagus. A 0.1 N hydrochloric acid solution and a normal salt solution are alternately infused through the catheter and into the esophagus, for example, at the rate of 8 mL/min for 10 min. The patient is unaware of which solution is being infused. If the perfusion with acid provokes the patient's usual pain and perfusion of the salt solution produces no pain, it, is concluded that the patient's pain is related to acid reflux. Using this objective method of assessment, complaints of discomfort to HCl perfusion were noted in 7% of normal subjects, 17% in Barrett's esophagus, 32% in GERD, and 58% in NERD patients. In the Examples, an animal model is used to demonstrate that compounds similar to DIPA-1-9 suppress the irritative effects of super-fused 0.1 N hydrochloric acid.

Dyspnea is a common symptom of disease and defined as "a sensation of difficult breathing" which includes sensations of choking and suffocation. As a sign, dyspnea is expressed as labored breathing and inadequate ventilation with a rise in plasma carbon dioxide tension. Dyspnea occurs in serious disorders such as pneumonia, congestive heart failure, asthma, chronic obstructive pulmonary disease, emphysema, cystic fibrosis, muscular paralysis or dystrophy, Parkinson's disease, lung cancer, debilitation from wasting diseases and the like. The sense of suffocation, encompassed in dyspnea, is a frightening experience. For example, in amyotrophic lateral sclerosus, 56% of patients experience dyspnea in the last month of life. Sleep apnea and snoring are also associated with uncomfortable breathing. Surprisingly, cooling of the upper aerodigestive tract with DIPA-1-9 syrup can relieve a sense of dyspnea. It is possible that cooling sensations from the pharyngeal and esophageal epithelium in proximity to the airways of the larynx and trachea convey a sense of fresh airflow.

Chest Pain and Differential Diagnosis of Chest Pain

Chest pain, accompanied sometimes by palpitations, sweating, shortness of breath, and choking sensations, is a common symptom that provokes a patient to see a physician or to seek admission to an Emergency Department. The physician's first priority on examining the patient is to determine if there are any life-threatening cardiovascular conditions. If warranted, a hospital admission for chest pain can be expensive because of work-up diagnostics such as serum enzyme assays, electrocardiograms, and radiotracer studies on heart function. It has been noted that noted that the median cost of a hospital admission for a patient with chest pain was US$7340 [Coley et al., Economic burden of not recognizing panic disorder in the emergency department. J. Emergency Medicine 36: 3-7. 2009]. Each year, approximately 6.4 million Americans visit the Emergency Department with complaints of chest pain and related symptoms, but only a small percentage exhibit an underlying cardiovascular etiology; the others have non-cardiac chest pain (NCCP). Chest pain is the second most common reason for an Emergency Department visit, the first reason being stomach and abdominal pain [see, e.g., Table 8 in Pitts et al., National Hospital Ambulatory Medical Care Survey: 2006 emergency department summary", National Health Statistics Reports, Vol. 7, pp. 1-38, 2006].

There are multiple causes of NCCP, including pectoral muscle strain, pulmonary disorders, indigestion, panic disorders, and, most frequently, esophageal dysfunction such as GERD [Amsterdam et al., Testing of low-risk patients presenting to the emergency department with chest pain: a scientific statement from the American Heart Association. Circulation, 122: 1756-1776, 2010]. Standard proton pump inhibitor drugs such as esomeprazole has very limited efficacy in suppressing unexplained chest pain and the onset of drug effect requires at least several days [Flook et al., Acid-suppressive therapy with esomeprazole for relief of unexplained chest pain in primary care: a randomized, double-blind, placebo-controlled trial, Amer. J. Gastroenterol., 108: 56-64, 2013].

A simple test with the DIPA-1-9 syrup, to distinguish NCCP from cardiac pain, may aid in the differential diagnosis of chest pains, permit triage of patients, and improve allocation of resources to reduce the costs of care. It is proposed here that an active ingredient such as DIPA-1-9, delivered onto the surface of the upper aerodigestive tract, may be useful for the relief of chest pain and aid in the differential diagnosis of chest pains.

Diseases of the Airways and Mucus Clearance

Diseases of the airways, such as chronic obstructive pulmonary disease, bronchitis, bronchiectasis, cystic fibrosis, and certain forms of asthma are associated with inflammation of airway mucosa and increased production of exudates. Exudates are normally removed by expectoration or swallowing. At night and during sleep, the pharyngeal muscles relax and clearance is inhibited, so exudates may accumulate in the oropharynx, and cause choking and gagging. A sensory agent that counteracts discomfort in the oropharynx and airways will be useful for such airway diseases because it can be utilized to help mucus clearance without hurting the throat lining via non-productive coughs.

Dysphagia and the Enhancement of Swallowing

There have been a limited number of attempts to treat the upper aerodigestive tract with sensory agents. It has been proposed to use sensory agents such as black pepper, lavender, capsaicin, capsids, and menthol to treat the dysphagia problems of the elderly [Ebihara et al., 2011]. These agents were applied as aerosolized liquid suspensions, or as a liquid delivered via a nasal tube to the pharynx. The exact sensory event for enhancement of clearance reflexes was not defined. Potent menthol and peppermint oil confectionery, such as Altoids®, are also sensory stimulants in the oral and nasal cavities. Menthol lozenges, weighing about 2.7 to 3.4 g each, and containing 5, 7, or up to a maximum of 10 mg of menthol in a sugar-dye matrix, are also sometimes used as oral stimulants, but have limited efficacy because of harsh taste. Certain N-alkyl-carbonyl-amino acid esters have been described for use in the treatment of throat discomfort and airway irritation [Wei, U.S. Pat. Nos. 8,426,463, 8,476,463].

Burning Mouth Syndrome (BMS)

BMS is characterized by persistent burning sensations on the tongue, accompanied frequently by taste alterations (Susana et al. 2017. Internat. J Dent. Res. Burning Mouth Syndrome-Latest Update. 1 (1): 14-23.; Grushka et al. 2002. Burning Mouth Syndrome. Amer. Family Physician 65: 615-620). Synonyms for this condition include "scalded mouth syndrome", "glossodynia" and "stomatodynia". Other sensations, namely, numbness, dryness, tingling and pain may occur throughout the mouth and tongue. Salivary secretion is not affected and there is no detectable pathological lesion on the tongue. The disturbed sensations most likely arise from dysfunction of nerves that supply afferents to the oral cavity: that is, the 5th, 7th, 9th and 10th cranial nerves. I find that DIPA-1-9, 10 mg/mL, sprayed into the mouth via a manually activated aerosol sprayer, delivering 0.07 mL per activation, will produce a robust cooling of the oral cavity. After 3 rapid activations, the contents are then spat out from the mouth, but the pleasant sensation of cooling will persist for ≥1 hr. There is a slight taste of bitterness, but it is likely that this aspect of DIPA-1-9 can be masked. I expect after experiment that BMS can be relieved with DIPA-1-9 delivered to the oral cavity. Some of the other DIPA compounds, such as DIPA-1-8 may also be effective with proper masking of the taste properties of the DIPA. Currently, BMS is a clinical challenge because of lack of effective treatment, although the condition is relatively benign.

Cough Hypersensitivity Syndrome (CHS)

CHS was defined by the European Respiratory Society as a condition in which the cough is caused by stimuli that don't usually cause cough, or a hypersensitivity to stimuli that are known to be tussive, e.g. citric acid or capsaicin. While this hypersensitive mechanism has been imputed initially in patients with chronic cough where no cause of the cough has been found, there is now evidence that even in patients with chronic cough associated with conditions such as asthma, chronic obstructive pulmonary disease, pulmonary fibrosis or gastroesophageal reflux disease, this mechanism is underlying the chronic cough. So, patients with CHS may have hypersensitivity to stimuli that do not usually induce coughing e.g. talking, laughing, going outside in cold weather or smelling perfume. Other common complaints are a sensation of having something stuck or irritating in the throat, and difficulty breathing such as a feeling that there is a blockage at the level of the throat and the patient can't get air into the lung. Most patients presenting with a chronic cough have CHS. An agent such DIPA-1-9 in syrup which "tones" down the sensitivity of the nerve endings should work for CHS.

In the context of the present discovery, the goals were to:
a) Identify and define an active compound with a precise sensory effect on the membranes of the upper aerodigestive tract that will produce a stimulus of coolness and counteract discomfort (irritation, itch, and pain). This sensation will not, of itself, produce discomfort but instead generate a sensation similar to when ice cream is swallowed but lasting longer. A sensation to avoid is a condition referred to as "cold discomfort".
b) Develop a topical formulation for localized delivery of the active compound onto targets of the nerve endings of the $9^{th}$ and $10^{th}$ cranial nerves.
c) Define a drug action with rapid onset (less than 1 min) and long duration (effective for at least several hours), with a dosage schedule that can be based on an "as needed" basis (pro re nata or p.r.n.), and thus allowing the patient to regain control of the sensory discomfort. Ideally, the active compound is sufficiently potent, with a unit dose of less than 10 mg per administration.
d) Use this medication for short-term (acute) and long-term (chronic) conditions to reduce hypersensitivity to irritant stimuli.

These objectives are met with a syrup formulation of DIPA-1-9 at a delivered volume of less than 1 mL per dosage with focused delivery onto the nerve endings of the $9^{th}$ and $10^{th}$ nerves.

Targeted Topical Delivery onto a Specific Location

To create a drug for topical delivery to the pharyngeal and esophageal surfaces requires understanding of target tissues and dynamics of the tissue environment. The neuronal receptive fields of the pharynx and esophagus linked to the afferents of the $9^{th}$ [glossopharyngeal], $10^{th}$ [vagus], and spinal afferents have an area of several $cm^2$, unlike the oral cavity which is at least 10× larger. So, a chewing gum containing DIPA-1-9 will not work, or a teaspoon of DIPA-1-9 in syrup, because the volume of 5 mL in a teaspoon is too large and the contents will transit through the pharynx and eosophagus before the DIPA-1-9 has opportunity to interact with its receptor.

The oropharynx is the arch-shaped structure at the base of the tongue, with the uvulva [or grape] hanging in the middle. The base of the arches, called the anterior pillars of fauces, is especially sensitive to cold sensations. If a cold metal probe is placed at this site in human subjects, cooling sensations and rapid swallowing movements are elicited [Kaatzke-McDonald, E. et al. The Effects of Cold, Touch, and Chemical Stimulation of the Anterior Faucial Pillar on Human Swallowing. Dysphagia 11:198-206, 1996]. The pharynx and laryngx surfaces are densely innervated by nerve endings of $9^{th}$ and $10^{th}$ cranial nerves [Mu and Sanders. Sensory nerve supply of the human oro- and laryngopharynx: a preliminary study. The Anatomical Record, 258, 406-20, 2000]. TRPM8 immunoreactive fibers are found in the lingual nerve of the tongue [Abe, J. et al. TRPM8 protein localization in trigeminal ganglion and taste papillae. Brain Research. Molecular Brain Research, 136: 91-8, 2005], and are abundant at the border of the oropharynx, and in the larynx, but not in the epiglottis [Sato, T. et al. The distribution of transient receptor potential melastatin-8 in the rat soft palate, epiglottis, and pharynx. Cellular and Molecular Neurobiology, 33:161-5, 2013]. The desired drug targets are the receptive fields of $9^{th}$ and $10^{th}$ nerve.

The throat is a term describing the region of the body around the voice-box. Internally, the relevant structure is the pharynx which is divided into three sections: naso, oro and laryngo. The nasopharynx, also called the rhinopharynx, lies behind the nose and above the level of the soft palate. The oropharynx reaches from the soft palate (velopharynx) to the level of the hyoid bone. The hypopharynx, also called the laryngopharynx. is in the space behind the larynx and reaches from the hyoid bone to the lower border of the cricoid cartilage. The oro- and laryngo-pharynx is a continuous funnel-shaped inverted trapezoid tube [Daniel et al., 2007] and the total surface area is about 10 to 15 $cm^2$.

The favored target for drug delivery is the lumenal surfaces of the oropharynx at the base of the pillars of fauces, and the lateral oropharyngeal walls. A secondary target is the lumen of the upper esophagus which is reached via the oropharynx.

The afferent signals to the brainstem from the oropharynx, and the laryngopharynx are primarily from the $9^{th}$ (glossopharyngeal) and $10^{th}$ (vagus) cranial nerves. The afferent signals from the receptive fields coordinate the clearance reflexes that empty the pharynx and protect the airways against entry of liquids and solids. For the upper esophagus, the innervation is from the vagus and spinal afferents. The targets for drug delivery are primarily the receptive fields of the $9^{th}$ and $10^{th}$ cranial nerves, and, to a lesser extent, the spinal afferents of the upper esophagus.

The oropharyngeal phase of swallowing occurs in the blink of an eye, in millisec, as the bolus moves from mouth to esophagus. The transit time, as measured by laser Doppler ultrasound or X-ray videofluorography is about 35 cm/sec [Sonomura et al., Numerical simulation of the swallowing of liquid bolus. J. Texture Studies 42: 203-211, 2011]. It is therefore difficult to deliver, adhere, glue, and retain a sensory agent on the surface of the oro-laryngopharynx. The active ingredient cannot be delivered as solid particles, as that would cause irritation and elicit coughing, so delivery of a agent in a syrup is the ideal method. An agent in a syrup spray will work, but a highly aerosolized spray may activate laryngeal receptors in simple epithelia and cause cough. An agent present as a solute in saliva is diluted in the mouth and still has to be in sufficient concentration to the contact the pharyngeal surface.

Onset, Duration of Action, and Schedule of Delivery

As contemplated here, the delivered agent for treatment should have a sensory effect with rapid onset of action, for example, within 1 min. The effects should be effective for at least one hour and preferably longer, otherwise the patient would have to repeatedly apply the drug to obtain relief. Preferably, there should be a "wow effect" of the active ingredient to stimulate sensory events. The patient should be able to identify this "wow effect" and use the liquid formulation on an "as needed" (p.r.n.) basis. With a fast onset of action, the patient should be able to be relieved of oropharyngeal and upper esophageal discomfort, and this relief will further reduce psychogenic factors (e.g., anxiety) associated with throat discomfort. These goals are achieved by DIPA-1-9 dissolved in a small volume of syrup applied to the base of the tongue.

Choice of Active Ingredient: Molecular Target, Specificity, Selectivity

There is a general view that the ion channel TRPM8 is the principal physiological element that transduces to the brain the cooling effects of agents such as menthol and icilin [McKemy et al., Identification of a cold receptor reveals a general role for Trp channels in thermosensation, Nature, 416, 52-58, 2002]. TRPM8 is a protein with 1104-amino acid residues and has six transmembrane domains. Activation of this receptor by decreasing ambient temperature results in the opening of a gate in the six transmembrane loops and non-specific cation entry into the cell. Depolarization of sensory neurons then transmit signals to the brain primarily via $A\delta$ (and some C) fibres. While this concept for the role of TRPM8 in sensory physiology may be valid for physical changes in temperature, the interpretation of the sensory effects of chemical agents such as menthol and icilin are more complex. Menthol not only stimulates TRPM8 in vitro, but also TRPV3, a receptor associated with warmth [Macpherson et al., More than cool: promiscuous relationships of menthol and other sensory compounds. Mol Cell Neurosci 2006; 32:335-343, 2006]. Menthol also inhibits TRPA1. Menthol is "non-selective" in its actions. Icilin stimulates not only TRPM8, but also TRPA1, and icilin inhibits TRPV3 [Sherkheli et al., Supercooling agent icilin blocks a warmth-sensing ion channel TrpV3. Scientific World Journal 2012; 982725, 2012] and glycinergic transmission [Cho et al. TRPA1-like channels enhance glycinergic transmission in medullary dorsal horn neurons. J Neurochem 122:691-701.2012]. Thus, menthol and icilin are "promiscuous" non-selective drugs and their actions may not be associated with any one particular receptor protein.

The correlation between a chemical's potency at the TRPM8 receptor (measured by the $EC_{50}$) and ability to evoke sensory events in the pharynx is complex. The applicant has studied many compounds covering a 100-fold range of TRPM8 potency, each of which exhibited full efficacy at the TRPM8 receptor, and evaluated their sensory effects. Surprisingly, a number of side-effects were observed with some of the compounds. For example, menthol produced chest discomfort at a dose of 5 mg in an orally dissolving tablet. By contrast, icilin did not produce cooling in the chest or the desired sensations on the throat. Among the DAPA compounds, the relationships of TRPM8 receptor potency to sensory events were not easily categorized. Firstly, the DAPA compounds with 6 to 8 methyl groups in the longest alkyl chain had strong aversive tastes in the oral cavity. Secondly, these 6 to 8 analogs caused icy cold pain and discomfort in the sternum. Surprisingly, DIPA-1-9, which has all of the desirable qualities for an ideal cooling agent on the oropharynx is not "super-potent" on TRPM8.

As shown in Study 4, the $EC_{50}$ [median effective dose] of a candidate for activating TRPM8 has little predictive value in identifying a candidate for treatment of sensory discomfort in the upper aerodigestive tract. This is not surprising and to over-interpret the $EC_{50}$ value is naïve. The 95% Confidence Limits of many $EC_{50}$ values overlap and are not easily differentiated from each other. The $EC_{50}$ values do not give information on the quality of the heat abstraction sensation, the duration of action, or the likelihood of unpleasant taste. Thus, identification of selective agents requires multiple bioassays and an optimized delivery system.

When it became clear that TRPM8 receptor potency screening could not be used as the primary method for selection of an active ingredient, it was necessary precisely define the distinct sensations of a test compound applied to the oropharyngeal surface. These descriptors are summarised in Table 4. For any compound, there may be some overlap in activity, but usually one compound occupies only one or two categories of sensations.

Cooling agents have different qualities in oral cavity and oropharynx. In the mouth, the gradations of cold are limited and are described as neutral, cold, or icy. In the throat, however, one can distinguish among the finer gradations of cool, refreshing cool, cold, and icy cold. Using the appropriate stimulus such as Haagen-Dazs ice cream, sherbert, and super-icy lemonade, these distinct levels are recognized as part of everyday experience. The varied sensitivity in the oropharynx is due to the dense topographical neuronal receptive fields. As the bolus transits downwards, the information transduced from the oropharyngeal surface are both the dynamic and static temperatures: that is, the brain "feels" $-\Delta$ ° C./t and not just absolute ° C. The mouth just "feels" the static temperature. Only an agent that simulates optimal $-\Delta$ ° C./t on nerve discharge will produce "refreshing cooling".

One aspect of the discovery here is that many of the compounds tested evoke sensations of intense cold and were painful to the throat. The sensations are akin to rapid drinking of cold water equilibrated with ice chips. The intense cold is accentuated if the drink is acidified, for example, with lemonade. The sensations of penetrating and intense cold on the surface of the oropharynx were uncomfortable, and aversive. The terms "icy cold" is used to describe this adverse event in the throat.

TABLE 4

Description of sensations and comments.

| Oral cavity | Descriptor | |
|---|---|---|
| | Taste | Sweet, sour, salty, metallic |
| | Cool and Cold | Limited range of sensitivity |

| Oropharynx | Descriptor | Heat abstraction sensations, analogy |
|---|---|---|
| Inactive | No effect | — |
| Cool | Cool | Drinking room temperature water |
| Ideal cool | Ideal cool | rich ice cream, such as Häagen-Dazs ice cream, smooth |
| Cold | Cold | Sherbert, can be numbing |
| Icy cold | Icy cold | Icy lemonade, painful, chest discomfort |

A second type of cold discomfort noted, for example, with DIPA-1-6, DAPA-2-6, and DAPA-2-7, was sensations of cold in the chest. The feeling of cold was behind the sternum and in the upper thorax. Most likely, the compound rapidly distributed and activated cold sensations in the eosophageal lining. The number of cell layers on the esophageal epithelium is less than that of the pharynx. These chest sensations were considered unpleasant by subjects, but may have some utility in counteracting the discomforts of heartburn and chest pain.

At higher oral doses (e.g., 5 mg or more) of DAPA-2-7, it was noted that there were sensations of cold on other body surfaces. The facial skin and the surface of the eyeball felt cool and cold. The surface skin of the scapula and the ankles also felt cool and cold, especially if there was a draft (increased airflow) in the room. The hands felt cold, as if the blood vessels were constricted. These sensations could have resulted from the systemic absorption of the DAPA-2-7 into the bloodstream. Alternatively, it is possible that strong coolness at one site may make the brain "generalize" the sensation, and attribute coldness to other parts of the body. These systemic sensations of cold, if not expected by the test subject, can alarm and be viewed as unpleasant.

Together, these three types of sensations—"icy cold" in the throat, coldness in the chest, and systemic coldness—is termed "cold discomfort". Cold discomfort limits selection of the active ingredient for an agent designed for localized action on the oropharynx/upper esophagus. The ideal agent must have a circumscribed site of action, and the intensity of the sensation should not cause "icy cold" in the throat, coldness in the chest, or systemic chills. Surprisingly and unexpectedly, DIPA-1-9 elicits this ideal cool in the oropharynx and esophagus but without cold discomfort.

When ice cream is placed in the mouth, there are pleasant cooling and sweet sensations on the tongue and on the walls of the mouth. When the ice cream is swallowed there is a brief robust refreshing sensation on the back of the mouth. This sensation in the upper throat can be replicated by repetitive swallowing or sipping of ice cream, or the equivalent sipping of a "milk shake" or "smoothie". An ideal sensation is replicated by swallowing a rich ice cream, such as Haagen-Dazs ice cream which, because of its high cream and low air content, abstracts heat at an optimal rate. This Haagen-Dazs type of ice cream sensation is optimal for treating upper aerodigestive disorders and relieving pharyngeal/esophageal discomfort. This sensation is called an "ideal cool" for reducing aerodigestive tract discomfort.

The pleasant ideal cool of DIPA-1-9 throat can be contrasted to the cold and icy cold sensations of rapid sipping of ice cold water or lemonade. To experience icy cold: Take a glass of water equilibrated, (after stirring) with ice chips—a temperature of about 4° C. Start sipping the water at the rate of about 1 sip per second. The first 5 sips are pleasant, but by 5 to 10 sips, the throat feels a dull cold, and after about 10 to 15 sips, the icy cold in the throat becomes unpleasant, and the sensations of icy cold can be felt in the chest, half-way down to the stomach. These unpleasant sensations constitute "cold discomfort".

Why are the sensations of sipping ice cream different from that of ice cold water? In both situations, the temperature of the contents in the throat is about the same, yet it is seldom possible to get unpleasantly cold in the throat with ice cream! One explanation is that the thermal conductivity of the oils and fats that make up ice cream is different from water. For example, the thermal conductivity value of olive oil is 0.17 W/m·K and that of water is 0.58 W/m·K. Ice water, with higher thermal conductivity (and higher thermal mass), abstracts more heat than ice cream. The rate of heat abstraction from the surface of the throat is then the determinant of the sensory perception and when it is too rapid or continuous, there is cold discomfort. On the other hand, a smooth heat abstraction rate produces a refreshing sensation.

Experimentally, an ice cream with a high cream content, such as Haagen-Dazs vanilla, works best for eliciting ideal cool. The pharmacological goal is then to identify a chemical sensory agent (i.e., a compound that does not abstract heat) that produces an ideal cool and not cold discomfort.

DIPA-1-9 elicits cool by action on receptive fields of afferents located in the pharynx. The sensory nerves include the facial ($7^{th}$)—innervating the surfaces adjacent to the palatine tonsils, the glossopharyngeal ($9^{th}$)—innervating the posterior of the tongue and walls of the oropharynx, and the vagus ($10^{th}$)—innervating portions of the lateral/posterior walls of the oropharynx and the laryngopharynx. Further down the aerodigestive tract, the upper esophagus is innerved by the vagus and spinal afferents. The distributions of these nerve fibers in pharynx are shown in FIG. 2 and constitute one set of targets for drug action.

Technical difficulties prevent direct measurement of sensory inputs from the receptive fields of the 7th 9th and $10^{th}$ nerves, but mapping has been done for the $5^{th}$ nerve, from receptive fields of the snout skin of rats. By inference, one can presume the processing of information is the same for all of these cranial nerves. The central response of the $5^{th}$ nerve neurons has been recorded and studied from rat superficial medullar dorsal horn that responds to innocuous thermal stimulation of the rat's face and tongue. Step changes of $-\Delta 5°$ C. stimulated cells with both static firing rates and cells that had mainly dynamic properties [Davies, S N et al. Sensory processing in a thermal afferent pathway. J. Neurophysiol. 53: 429-434, 1985]. Similar studies in cats and humans showed that step decreases in temperatures (dynamic changes), as low as A $0.5°$ C./sec, were readily detectable by neurons and by psychophysical measurements [Davies, S N et al. Facial sensitivity to rates of temperature change: neurophysiological and psychophysical evidence from cats and humans. J. Physiol. 344: 161-175, 1983]. From a study of the spike patterns of neuronal discharge (impulses/sec), it was clear that dynamic and not static firing responses to a change in temperature were the most powerful stimuli for generating coolness/cold sensations [see, e.g., Davies et al. 1983]. That is, the brain "sees" $-\Delta°$ C./t and not absolute $°$ C. Thus, an agent that simulates optimal $-\Delta°$ C./t on nerve discharge will produce "ideal cool". Thus, one can see why cool temperature sensing in the static conditions of the oral cavity are different as the bolus of liquid transits through the lumen of the pharynx and esophagus.

Delivery to Target: Place and Right Concentration

In this invention, the goal is to apply DIPA-1-9 in a small volume syrup onto the receptive fields of the $9^{th}$, and $10^{th}$ cranial nerves to counteract irritation, itch, and/or pain in the pharynx and esophagus. The fast transit time (~35 cm/sec) of solids/liquids through the oropharynx is a hindrance to topical drug delivery to the receptive fields, but this obstacle can be circumvented by formulation of the active ingredient into a milieu that coats the target. This is especially achieved when DIPA-1-9 is delivered as liquid solution in syrup.

The DIPA-1-9 dissolved in a syrup, and having liquid miscibility and chemical stability, is ideal for delivery as a focused liquid aliquot. These methods of liquid delivery may also be convenient for individuals who are unable easily to use solid dosage forms, e.g. young children, the elderly, and disabled individuals with difficulties in salivating or swallowing. By using a syrup the liquid formulation is uniformly dispersed and adheres with increased contact time on the pharynx and avoids rapid transport down into the esophagus.

A preferred formulation is a DIPA-1-9 formulation in a syrup at a concentration of 5 to 15 mg/mL and administered as single unit aliquots of 0.5 to 1.0 mL onto the base of the tongue. Such a formulation exerts a sensory effect in less than 2 min and is effective for several hours for throat discomfort and heartburn. A preferred liquid formulation is 8 mg/mL of DIPA-1-9 dissolved in simple syrup or cherry syrup (Humco Compounding, Austin, Tex.). This solution can be placed in a plastic vial and administered to the back of the mouth. Alternatively, the syrup may be place in a reservoir bottle with a manually activated spray pump with a spacer attachment of 3 inches (~7.5 cm) that will facilitate delivery onto the surfaces at the back of the mouth. Another possible formulation is the use of quick-dissolving liquid gel or film that can be placed in the back of the mouth, at the base of the tongue.

The schedule of delivery of the agent is designed for an "as-needed" basis by the patient, and not as a fixed-interval drug. By this therapeutic strategy, the individual resumes voluntary control of upper aerodigestive discomfort, and can, for example, sleep better at night, gain peace of mind, and have less anxiety. Alternatively, in the treatment of the cough hypersensitivity syndrome, when the objective is to reduce neuronal hypersensitivity, a fixed interval regimen also works well.

Study 1

Agonist Potency and Selectivity on TRP channels: TRPM8, TRPV1, and TRPA1

In the first set of data, the potency and in vitro effects of test compounds were evaluated on cloned hTRPM8 channel (encoded by the human TRPM8 gene, expressed in CHO cells) using a Fluo-8 calcium kit and a Fluorescence Imaging Plate Reader (FLIPR$^{TETRA}$™) instrument. The assays were conducted by ChanTest Corporation (Cleveland, Ohio 44128, USA). Test solutions were in a HEPES-buffered saline, in 384-well plates, and placed into the FLIPR instrument (Molecular Devices Corporation, Union City, Calif., USA). Four 4 to 8 concentrations were tested, with L-menthol as the positive control. The test cells were Chinese Hamster Ovary (CHO) cells stably transfected with human TRPM8 cDNAs. Concentration-response data were analyzed via FLIPR Control software) and fitted to a Hill equation for the $EC_{50}$. The 95% Confidence Interval was obtained using GraphPad Prism 6 software.

The results (agonist activity in the TRPM8 receptor assay) are summarized in Table 5. All tested compounds showed full efficacy, i.e. at the highest tested concentration there was ~100% stimulation of calcium entry, and the data fitted a sigmoidal dose-response curve. The $EC_{50}$ of the more potent sensory compounds DIPA-1-6 to 1-9, and DIPA-2-5 to 2-8 fell within a narrow range with overlapping 95% Confidence Intervals. There were no distinguishing features in the $EC_{50}$ which enabled prediction of the compounds with desired cooling properties in the upper aerodigestive tract. The structural modifications of 3-1 and 3-2 resulted in a significant loss of bioactivity.

In a second set, tests were made on "mixed" isopropyl-sec-butylphosphorylhexane and heptane analogs described as 3,4-6 and 3,4-7 in Table 2, and results shown in FIG. 4. The data were collected by Andersson et al. of King's College, London, UK, using his methods described in "Modulation of the cold-activated channel TRPM8 by lysophospholipids and polyunsaturated fatty acids. Journal Neuroscience 27 (12): 3347-3355, 2007. Here, the cellular entry of the calcium-sensitive dye Fura-2 was used to study the effect of the test compounds on TRPM8 expressed in Chinese hamster ovary cells. Cells, grown in culture, were seeded at an approximate density of 30,000 cells/well overnight, and loaded for ~1 hr with 2 M Fura-2 (Molecular Probes, Leiden, The Netherlands), and then placed on glass coverslips. Test solutions were added with a micropipette positioned close to the cells. Emission intensity from cells was measured for 90 sec, at every 4 or 5 sec, using excitation wavelengths of 340 and 380 nm and an emission of 520 nm. Fluorescence emission intensity ratios at 340 nm/380 nm excitation (R, in individual cells) were recorded with a FlexStation and the ImageMaster suite of software (PTI, South Brunswick, N.J.). Samples were tested in triplicate at each concentration and the averaged values analyzed by non-linear regression using an a sigmoidal function fit of the points to obtain an estimated EC50 (median effective concentration) (GraphPad Prism software, La Jolla, Calif.).

TABLE 5

TRPM8 agonist activity of test compounds.

| Compound | $EC_{50}$ (µM) | 95% Confidence Interval | Relative Potency to L-menthol |
|---|---|---|---|
| Menthol | 3.8 | 2.5 to 5.6 | 1.0 |
| DIPA-1-5 | 5.6 | 4.4 to 7.2 | 0.7 |
| DIPA-1-6 | 2.4 | 1.5 to 4.0 | 1.6 |
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 TO 2.5 | 4.0 |
| DAPA-2-4 | 14.5 | 7 to 29 | 0.3 |
| DAPA-2-5 | 1.7 | 1.0 to 2.9 | 2.2 |
| DAPA-2-6 | 0.8 | 0.5 to 1.3 | 4.7 |
| DAPA-2-7 | 1.1 | 0.6 to 2.3 | 3.4 |
| DAPA-2-8 | 1.3 | 0.7 to 2.3 | 2.9 |
| DAPA-3-1 | 24 | 8 to 76 | 0.2 |
| DAPA-3-2 | 4.2 | 1.6 to 10.8 | 0.9 |

The potency of three analogs for activation of TRPM8 (cooling receptor) in transfected cells is shown in FIG. 4. The units (Δ ratio) on the ordinate measure entry of fluorescent calcium probes into transfected cells. The 3,3-7 (DIPA-1-7) is substantially more potent (~10× and ~5×) than 3,4-6 and 3,4-7. Note that 3,4-6 and 3,4-7 species do not reach the same degree maximal efficacy on activation of the receptor, even at supra-maximal concentrations.

FIG. 4. is a graph of fluorescence response (Δ ratio 340/380) in TRPM8 transfected cells as a function of the logarithm of the concentration of the test compound, expressed in µM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and polyunsaturated fatty acids. Journal Neuroscience 27 (12): 3347-3355, 2007.

In a third set, the selectivity of the test compounds on TRPM8, TRPV1 channels (human TRPV1 gene expressed in HEK293 cells) and TRPA1 channels (human TRPA1 gene expressed in CHO cells) were examined.

The selectivity of DIPA-1-9 on TRP channel receptors, TRPM8, TRPA1 and TRPV1 is shown in FIG. 3 of Yang et. al. A novel TRPM8 agonist relieves dry eye discomfort. BMC Ophthalmology (21017) 17: 101, and incorporated herein by reference. The applicant is a co-author of this publication. This selectivity is also seen with DIPA-1-7 and DIPA-1-8 (data in FIG. 1, Wei U.S. Pat. No. 9,956,232). For these results, the test cells were Chinese Hamster Ovary (CHO) cells or Human Embryonic Kidney (HEK) 293 cells transfected with human TRPV1 or TRPA1 cDNAs. The positive control reference compound was capsaicin (a known TRPV1 agonist) or mustard oil (a known TRPA1 agonist).

In summary, the relative potencies of these test series, as measured by the TRPM8 $EC_{50}$ [median effective dose], seem to have limited predictive value for comparisons. The 95% Confidence Limits of many $EC_{50}$ overlap and only analogs with at least a 5-fold difference in potency are clearly distinguishable from each other. To select an ideal ingredient, it is necessary to identify the best cool ingredient and avoid icy cold sensations and adverse tastes. Furthermore, the duration of action is an important parameter. But the $EC_{50}$ does not give information on the quality of the heat abstraction sensation, the likelihood of unpleasant taste, or the duration of drug effect. Thus, desirable drug actions (access to and efficacy at TRPM8) are not defined by the $EC_{50}$. To over-interpret the $EC_{50}$ is naïve. Other bioassays are required to address the questions of selectivity and specificity. The 3,4-6 and 3,4-7 analogs described as the most active in '496 had weak TRPM8 potencies.

Study 2
Skin Irritation Tests

In pre-clinical studies DIPA-1-9 was found not to be irritating when applied to the shaved rat skin at up 20 mg/mL. Injected subcutaneously into the anesthetized rat, DIPA-1-9 did not affect blood pressure or heart rate. DIPA1-9 was applied to the eyelids of patients with dry eye disorder and found not to be irritating. By contrast, DAPA-2-6 and DAPA-2-7, in undiluted form, are both skin irritants. Pure DIPA-1-9 applied to the abdominal skin of anesthetized rat at 20 µL did not cause significant inflammatory response. These results gave greater confidence in the selection of DIPA-1-9 for further testing.

TABLE 6

Irritant activity of test compounds on rat skin.

| Compound | Mol. Wt. | Redness after 20 µL applied topically to skin (scale of 0 to +++) |
|---|---|---|
| DIPA-1-9 | 260 | 0 |
| DAPA-2-6 | 246 | + |
| DAPA-2-7 | 260 | ++ |

Study 3
Topical Permeation of Embodiments

To further study the skin permeation of DIPA compounds, tests were conducted on the flux of DIPA-1-7 and DIPA-1-9 through excised hairless mouse skin in vitro. These tests were conducted by Prof Choi, Dean of the School of Pharmacy of Chosun University, Korea, and the results shown in (FIG. 5).

FIG. 5. shows the flux of DIPA-1-7 and DIPA-1-9 through excised hairless mouse skin in vitro. Test chemicals dissolved in a gel were placed in an incubation well for 8 hr and the permeated amount of the chemical measured by a high pressure liquid chromatograph equipped with a refractive detector. These tests were conducted by Prof Choi of Chosun University, Korea. The flux of DIPA-1-7 was ~5× greater than DIPA-1-9. Standard enhancers with polyhydric alcohols, such as a propylene glycol-oleyl alcohol mixture (50:50) or Lauroglycol 90, designed to increase permeation added to the DIPA-1-7 gel decreased the rate of permeation by ~50%, indicating the importance of water solubility for permeation.

Standard enhancers with polyhydric alcohols, such as a propylene glycol-oleyl alcohol mixture (50:50) or Lauroglycol 90, designed to increase permeation added to the 1-7 gel decreased the rate of permeation by ~50%. This was not expected, and excipients are usually added to formulations to increase absorption and penetration. DIPA-1-7 was very active in penetrating the excised skin. This explains its potent action in producing cold discomfort.

FIG. 5. shows the flux of DIPA-1-7 and DIPA-1-9 through excised hairless mouse skin in vitro. Test chemicals dissolved in a gel were placed in an incubation well for 8 hr and the permeated amount of the chemical measured by a high pressure liquid chromatograph equipped with a refractive detector. These tests were conducted by Prof Choi of Chosun University, Korea. The flux of DIPA-1-7 was ~5× greater than DIPA-1-9. Standard enhancers with polyhydric alcohols, such as a propylene glycol-oleyl alcohol mixture (50:50) or Lauroglycol 90, designed to increase permeation added to the DIPA-1-7 gel decreased the rate of permeation by ~50%, indicating the importance of water solubility for permeation.

The importance of water solubility for permeation was further illustrated in studies on the abdominal skin of anesthetized rat. Pure DIPA-1-7 applied on the skin caused vigorous shaking, but pure DIPA-1-9 was not active. The pharmacokinetic determinants of bioactivity are precise. Thus, for the avoidance of cold discomfort, DIPA-1-9 has to reach the receptors in the stratum basale but not "overstimulate".

Moreover, it has to reside at the target site for a sufficient duration to produce the desired pharmacological endpoints.

Study 4

Sensory Qualities of Compounds Applied to Oral Cavity and Pharynx

Tests were on four volunteers, with 3 to 5 trials per substance. Compounds were prepared in cherry-flavored syrup at 5 mg/mL and administered ~0.8 mL per dose with a 2 mL plastic vial to the base of the tongue. The subjects asked to rate the sensations for cooling intensity, cold discomfort and adverse taste. Surprisingly, the sensory results were clearcut and there were no ambiguities about the sensory effects that were elicited. The compounds DIPA-1-7, DIPA-1-8, DAPA-2-6, DAPA-2-7 and 3,4-7 produced cold, icy cold, and adverse tastes which were instantly recognized and disliked. In particular, DIPA-1-7 produced icy pain in the back of the throat and was considered aversive. 3,4-6 produced robust cooling, but its duration of action 5 to 10 min, were too short to be of therapeutic value. By contrast, DIPA-1-9 syrup produced a coolness and cold which was well-tolerated and the concentration could be increased to 15 mg/mL without objections: that is, there was no pain or discomfort.

TABLE 7

Sensory activity of compounds tested as a
5 mg/mL solution in cherry-flavored syrup.

| Compound | Sensation | Discomfort | Adverse Taste |
|---|---|---|---|
| DIPA-1-7 | painful cold | +++ | +++ |
| DIPA-1-8 | cold | ++ | ++ |
| DIPA-1-9 | cool | 0 | 0 |
| DAPA-2-6 | icy cold | ++ | ++ |
| DAPA-2-7 | icy cold | +++ | +++ |
| DAPA-2-8 | cold | ++ | ++ |
| 3,4-6* | cool | + | 0 |
| 3,4-7 | painful cold | ++ | + |

*short duration of action of 5 to 10 min, precludes use

The unpleasant tastes produced by DIPA-1-7, DIPA-1-8, 2-6, 2-7, and 2-8 were described as "metallic", "organic solvent-like", and "harsh" which lasted for at least 15 min. The subjects said these taste qualities were unpleasant and undesirable. When tested in the evening near sleep time, the perception of cooling in the throat was more pronounced presumably because there were fewer environmental cues for distraction. In these situations, the heat abstraction sensations were perceived for ≥20 min. Although overt cooling sensation may not be felt after 15 min, the general sense of refreshment in the throat from DIPA-1-9 may persist for 3+ hours. Surprisingly, increasing the test concentration of DIPA-1-9 from 5, to 8 to 15 mg/mL in simple syrup and a volume of 0.8 mL per dose did not produce icy cold or pain. Thus, there is a safety margin in the use of DIPA-1-9 without risks of a painful throat.

The unexpected observation here was DIPA-1-9 has good qualities of cooling sensation. But in the other analogs, where the alkyl chain is n-hexyl, n-heptyl, or n-octyl, the chemicals cause cold discomfort and adverse taste (FIG. 7). Furthermore, the duration of action DIPA-1-9 was sufficiently long to be of clinical value. Thus, these trials showed, surprisingly, that DIPA-1-9 is uniquely the best ingredient for sensory discomfort in the pharynx. The qualitative differences in DIPA-1-9 that makes it selective and exceptional could not have been predicted from prior art. It was concluded that DIPA-1-9 is the best candidate as an antinociceptive agent for the upper aerodigestive tract.

FIG. 7. shows a comparison of the sensory effects of DIPA-1-7, DIPA-1-8, and DIPA-1-9 administered to the base of the tongues of 4 volunteers using a 2 mL vial for delivery. The concentration of the DIPA compounds was 5 mg/mL in cherry-flavored syrup administered in a volume of 0.8 mL per dose. The sensory effect were recorded every 5 min for 1 hr.

The 1-di-sec-butyl-phosphorylpentane (DAPA-8) was also tested in syrup, but its duration of action was too short to be of practical value. Like 3,4-6 its duration of action was about 5 to 10 min. It is possible that DIPA-1-8 will be a better agent than DIPA1-9 for situations where there is excess exudate (mucus and phlegm) in the trachea, larynx, pharynx, and esophagus, because DIPA-1-8 can more easily reach the TRPM8 receptors in stratum basale than DIPA-1-9.

Study 5

Pre-Clinical Studies in Rat Model of Swallowing Movements

A principal endogenous irritant in the linings of the upper aerodigestive tract is hydrochloric acid. Acid stimulations of the mucosa of the pharynx will elicit reflex swallowing. Receptive regions are in the pharyngeal walls and innervated by the glossopharyngeal nerve ($9^{th}$) and the interior superior laryngeal nerve ($10^{th}$). In a rat animal model, solutions of organic acids such as acetic acid and citric acid were effective in eliciting swallowing [Kajii et al., Sour taste stimulation facilitates reflex swallowing from the pharynx and larynx in the rat Physiology & Behavior 77: 321-325, 2002]. These methods for measuring sensory responses to acid can be adapted for screening the activity of DIPA-1-9. An agent that stimulates swallowing or an agent that suppress the acid challenge may then have utility in relieving dysphagia or the discomfort of heartburn, respectively. Preliminary experiments were conducted at the Pavlov Institute of Physiology, St. Petersburg, Russia, using adult male Wistar rats (see Table 11) and Wei (US 0.2015/0111852 A1). Swallowing movements was identified as the electromyogram activity and could also be visualized as laryngeal movement. Examples of results are shown in Table 8. Work is in progress to get more results for DIPA-1-9. I predict that DIPA-1-9 will stimulate swallowing at low doses and inhibit acid stimulated swallowing at higher doses.

TABLE 8

Potency of various analogs for the suppression of acid-induced swallowing movements in the anesthetized rat

| Code | $EC_{50}$ ± S.E.M. (mg/mL) | Relative Potency | Comments | TRPM8 Relative Potency |
|---|---|---|---|---|
| DAPA-2-7 | 0.20 ± 0.02 | 0.45 | long-lasting; > ~30 min | 0.64 |
| DAPA-2-8 | 0.56 ± 0.17 | 0.16 | — | 0.71 |
| DIPA-1-7 | 0.82 ± 0.08 | 0.11 | — | 1 |
| DAPA-2-6 | 1.7 ± 0.7 | 0.05 | — | 0.87 |

Study 6
Pre-Clinical Studies of Mouse Cough Model of Upper Respiratory Tract Infection This study was conducted at the State Key Laboratory of Respiratory Disease, Guangzhou Institute of Respiratory Disease, Guangzhou Medical University, Guangzhou, China The investigators were Ren Nee, Dong PeiJian, Liu ChunLi, Zhang Qingling, Wei TakFung, and Zhong NanShan. The methods used described earlier. Ye X M et al. Zhonghua Yi Xue Za Zhi. (2011) 91(24):1708-12. [A guinea pig model of respiratory syncytial virus infection for cough and its neurogenic inflammatory mechanism] Chinese. Ye X M et al. Cough reflex sensitivity is increased in guinea pigs with parainfluenza virus infection. Exp Lung Res. (2011) 37(3): 186-94.

Mice were used instead of guinea pigs. The experimental procedures were approved by the Institutional Animal Care and Use Committee.

Briefly, mice were intranasally inoculated with respiratory syncytial virus (RSV) and the cough count monitored with an Buxco system (Buxco, Wilmington, N.C., USA). The dosing parameters were as: 25 μL intranasal instillation per mouse for saline and DIPA-1-9 (20 mg/mL), 0.1 mL per mouse for perioral codeine, 10 mg/mL. Cough counts were measured 10 min after saline or DIPA-1-9 and 1 hr after codeine. Cough frequency was detected as a transient change in airflow pressure in a chamber and the signal recorded via a pressure transducer and computer. Additionally, the audio-amplified count was also recorded electronically. Coughs were counted for the 6 min. The experiment was visually monitored by the investigator. As shown earlier, peak cough frequency approximately 2 weeks after inoculation, when viral replication and airway pathology is verified by RSV RNA measurements, cytology and histopathology. The course of airway inflammation diminishes by 4 to 7 weeks after inoculation and mimics human respiratory tract infections.

FIG. 8. shows DIPA-1-9 inhibits cough frequency in a mouse model of respiratory tract viral infection. Mice (n=4 to 6 per group) cough more frequently (black bars) after inoculation with respiratory synctial virus (RSV). Codeine administered 1 mg perioral (p.o.) per mouse, or DIPA-1-9 0.5 mg in 25 pt intranasally (i.n.) per mouse, significantly inhibited cough frequency (*P≤0.01 and ≤0.05 for the three time periods of testing, Dunnett's test for multiple comparison). These results in mice show that DIPA-1-9 has potential antinociceptive activity in the upper aerodigestive tract.

Case Studies

The rationale and data set for selecting DIPA-1-9 in syrup as a treatment agent for upper aerodigestive discomfort have been described. In the case studies reported herein, the efficacy of DIPA-1-9 was investigated in volunteers for: a) control of acute cough, b) control of chronic cough, c) control of cough hypersensitivity, d) facilitation of mucus expectoration in a case of productive cough, e) control of satiety and indigestion induced chest discomfort, f) attenuation of acid-induced reflux discomfort, g) facilitation of swallowing, h) reduction of the sense of dyspnea during insomnia.

These general effects were consistently observed: a rapid onset (≤1 min) of the sensation of coolness in the throat after application of DIPA-1-9 syrup to the base of the tongue. The coolness spreads to the rest of throat and intensifies, as if a spoonful of rich ice cream had been swallowed. This cooling effect lasts for ≥15 min, and any prior discomfort in the throat is relieved. The cooling sensation can be used to facilitate mucus expectoration from the airways. Also relieved is the sense of suffocation when lying down to sleep in a subject that has dyspnea. The syrup does not have adverse tastes or produce cold discomfort behind the sternum.

Case 1.

Two cases of subjects with cough variant asthma (CVA) are described here. CVA is a type of asthma in which the main symptom is a persistent non-productive cough, i.e. a cough that does not produce mucus. The cough, by definition of the condition, persists for at least 8 weeks and may be aggravated by such conditions as dry, smoky air, or respiratory tract infections. Treatment with normal asthma medications such as inhaled steroids and beta-adrenergic agonists (to relax bronchial smooth muscle) have limited value in reducing the cough.

The first subject was a 25-year old male working in a diner serving kebabs and grilled meat in the South of France. Business was good but he worked in a smoky environment and over time developed a persistent cough that lasted for 6+ months. He was diagnosed as having CVA, but standard medications for asthma did not affect the frequency of coughing which was constant, debilitating, and affected his ability at work. He was distressed because his physician's advice was not working.

The subject agreed to try the cough syrup and was given a packet of 20 vials, each vial containing 1 mL of DIPA-1-9, 8 mg/mL dissolved in cherry-flavored syrup. He was instructed to use the vials on an as needed basis to reduce the urge to cough, but not to exceed 3 vials per day. Surprisingly, the subject noted that the cough frequency went down within 3 days of use and was not bothersome after one week. He asked for a continued supply of the vials which was given to him, but after one month the subject declared that the coughing problem had disappeared. He was most grateful for the opportunity to try the DIPA-1-9.

A 72-year old male, prominent in business circles in Hong Kong, developed a persistent cough. He was a smoker and had allergic rhinitis, but did not manifest wheezing upon exertion. He was misdiagnosed as having tuberculosis, and put on a course of isoniazid and other drugs but he lost weight and became apprehensive about his future. His cough occurred spontaneously and did not need triggers, but the cough frequency increased with socializing, with drinking, laughing and speaking. This cough was present for 3+ months and did not to go away. His doctor changed his diagnosis to asthma and prescribed Singulair, but this did not work. After a particular embarrassing episode, when he coughed violently after eating a piece of Szechuan pepper fish during a banquet, the subject volunteered to try an experimental remedy. He was given two packets of DIPA-1-9 vials, each vial containing ten 1 mL of DIPA-1-9, 8 mg/mL in simple syrup. He consumed the vials within 5 days and asked for more. This regimen was repeated for another 5 days, and surprisingly the cough was gone. He said that he had always been skeptical of academic scientists because such people did not seem to him to do anything significant, but this time he was happy to participate in an experiment.

In these two cases of chronic cough, DIPA-1-9 in syrup appeared to act by reducing the cough hypersensitivity syndrome: i.e. over time the nerve endings became less sensitive to tussive stimuli. The subjects became more optimistic as the coughing urge and frequency was brought under control. They became less paranoid about progression of illness. Their ability to socialize increased. The ability of the DIPA-1-9 syrup to relieve throat discomfort was self-evident and robust.

Case Study 2

A 50-year old male scientist received an award to conduct a 6-month research project in GuangZhou, China. He was rented a hotel room and lived alone. He used the public subway and, in the fall, he "caught the flu" with a 3-day fever and throat discomfort, chills and coughing. He developed a "productive" cough with thick mucus, which gradually thinned out after about a week, but the cough persisted and increased in frequency, until his throat felt raw. He did a count and reported an averaged of 25 to 40 coughs per hr, with the higher frequency at night. He could not sleep well because lying down on the bed exacerbated the itch in his throat and increased the urge to cough. Because he worked in the laboratory, he had access to the DIPA-1-9 syrup (Simple Syrup, 8 mg/mL stored 0.8 mL per plastic vial) and began to experiment on himself. He took the syrup on an as needed basis for three successive days and used two to three vials per day. He said that the cough frequency went down to an average of 5 to 10 coughs per hour. He said he slept better than he had in the two preceding weeks. He remarked that he learned how to utilize the DIPA-1-9 syrup to help expectorate mucus in his airways. He said that: "Instead of letting the itch in my throat stimulate non-productive coughs, I will make use of the cooling effect of the syrup to suppress the urge the cough until I could feel a lump of mucus accumulate in my throat. Then I will go to the bathroom, stand over the sink, braced myself with my arms on the rim of the sink, and heave out the phlegm. The coolness in my throat allowed me to this without significant discomfort to my throat lining. A second method of heaving was to stand over the toilet, place my hands on top of my upper legs and heave into the toilet. Getting rid of the mucus felt good! It was particularly important in helping me having a good night's sleep." After using the syrup for 5 days, the cough and throat discomfort disappeared.

This case illustrates the value of the DIPA-1-9 syrup in helping the subject expectorate phlegm. Mucus clearance is an important therapeutic goal in the treatment of airway inflammation. If the airway inflammation cannot be ameliorated then the mucus accumulation exacerbates the airway injury and threatens the patient's life. The progressive movement of mucus towards the larynx triggers the cough. But frequently the cough is "not efficient", i.e. it does not remove the mucus, and the throat lining becomes raw and painful from the coughing effort. The cooling actions of the DIPA-1-9 enable the subject to suppress the urge to cough until there is sufficient mucus to expectorate. Thus, the efficiency of mucus clearance is increased.

Case Study 3

A retired clinical pharmacologist worked at an out-patient clinic and consulted patients with respiratory problems. He frequently saw patients with cough, and he was atuned to current research, but he felt that the pipeline drugs were probably too costly for the treatment of acute cough. He volunteered to test the DIPA-1-9 formulations after obtaining informed consent from his subjects. Over a 3-month period, he recruited and made observations on 10 subjects with cough using a standardized questionnaire. There were 3 M, 7 F in the group, average age of 46 years, with cough of: unknown etiology (4), post-infectious cough (4), one bronchitis, and one eosinophilic bronchitis. Subjects were given a sprayer containing DIPA-1-9, 5 mg/mL in cherry flavored syrup, and a questionnaire to self-report cough frequency over a period of 1 week. At the end of the test period, the subjects reported that the medication was: very effective (3), partially effective (4), and not effective (3). All 3 of the "not effective" subjects came from the cough of "unknown etiology".

Case Study 4

Three over-weight individuals liked to over-eat and had frequent bouts of indigestion discomfort, precipitated by excess of pizza, ice cream, drinks, and a recumbent position on the sofa. The signs and symptoms usually consisted of burping and belching, nausea, and acid tastes in the throat. The subjects found that the discomfort of satiety was instantly relieved by application of DIPA-1-9, 8 mg/mL in simple syrup, to the base of the tongue. The reliable response was that the sense of excess fullness went away and "I feel better, and not stuffed up". On another occasion an individual had hiccups after swallowing food too fast. These hiccups were stopped immediately by taking a vial of DIPA-1-9 syrup.

Case Study 5

A distinguished Professor of Pharmacology and Respiratory Medicine became interested in the use of cooling agents for cough and for clearance of airway mucus. In his group of 10 graduate students and post-doctoral fellows, 5 had episodes of coughing and found the DIPA-1-9 syrup combination to be clearly efficacious in the treatment of their coughing discomfort. One graduate student even tested it on her grandmother and found that it worked. Asked to comment on the mechanisms of action of DIPA-1-9, the Professor noted: "The primary goal is always to have the right molecule delivered to the right place at the right dose. Here, placement of DIPA-1-9 on the receptive field of the $9^{th}$ nerve is important. Direct delivery to the $10^{th}$ nerve afferents will most likely evoke coughing. It is well-known that cold air will evoke coughing in asthma patients, and this is a $10^{th}$ nerve phenomenon. Using the syrup and avoiding aerosol droplet contact to the laryngeal afferents in an imaginative step. If the DIPA-1-9 syrup works, it will be a significant advance, but don't expect too much credit. People will say it is obvious because menthol lozenges are used for cough. On the other hand, I think menthol lozenges work because they are sweet, and the sweetened saliva has to be constantly swallowed. In a menthol lozenge it is the swallowing of the sweetened saliva that stops the cough, not the cooling actions of menthol which is very limited."

Case Study 6

A 65-year old overweight male was under stress from business difficulties and from an excessive gambling habit. After a gargantuan meal with friends in which he drank several glasses of Johnnie Walker blue label, he spent several hours at the dice table in a casino. Later in the evening in his hotel suite, he complained of chest pains and tightness in the chest, of pain behind the sternum, and a shortness of breath. He felt an acid taste in his mouth and took a Tagamet and then a Zantac tablet. The chest pain persisted and he felt anxious, flushed, and sweaty. He worried that "the end might be near" and debated calling 911, but did not want to create a scene at the hotel. He decided to try some DIPA-1-9 syrup, stored in small plastic vials, each containing 0.5 ml of 8 mg/mL of DIPA-1-9. These vials had been given to him previously, with the suggestion that it might help his indigestion. He placed the contents of two vials in rapid succession on the base of his tongue and swallowed. He said the sensation was that of cool water entering his throat and chest. The coolness was not strong, but gradual and penetrating. The pain behind his sternum quickly diminished and he felt more comfortable and less agitated. His breathing became normal. He fell asleep and did not wake till the next morning. He then went to see his personal physician who measured his serum troponin levels which was found to be within normal limits. His physician advised him to watch his diet and weight and not to gamble. Otherwise, his doctor thought his heart was healthy.

In this case, it seems that the symptoms of indigestion [non-cardiac pain] can be confused with chest pains caused by inadequate oxygenation of the heart muscle [e.g. angina or cardiac pain caused coronary arteries disorders]. The availability of the DIPA-1-9 syrup, with its rapid onset of action, allowed the non-cardiac pain to be relieved, and thereby avoid an unnecessary trip to the hospital emergency room.

Case Study 7

A 75-year old retired engineer had Parkinson's disease for 20 years. He had the best medical care which included brain stimulation of the thalamus but in the past two years his motor abilities deteriorated and he complained of poor sleep, muscle rigidity, and difficulty in chewing and swallowing food, but his most distressing symptoms were labored breathing and panic attacks arising from thoughts of suffocation. He volunteered to use the DIPA-1-9 syrup, 8 mg/mL stored 0.8 mL in a plastic vial, before going to sleep. His wife immediately noticed that he fell asleep quickly and slept without interruption until morning. The subject continued to use the DIPA-1-9 on an as-needed basis. He said the syrup gave him a refreshing sensation in the throat and a sense of relaxed breathing of cool air without effort. He could chew and swallow his food comfortably. The fear of suffocation at night disappeared. His panic attacks have also not reappeared.

In summary, the concept has been put forward that heat abstraction sensations, captured by topical application of a molecule, can be used to alleviate discomforts of the aerodigestive tract, specifically the lumens of the pharynx and eosphagus. By synthesizing compounds and devising tests, a molecule named DIPA-1-9 was identified as having the selective properties for achieving the desired sensory effect: namely, an ideal cool equivalent to that of a spoonful of a rich ice cream, such as Haagen-Dazs ice cream, on the throat. On receptor targets, DIPA-1-9 was selective for TRPM8 and not TRPVI and TRPA1. When bioassayed in mice, DIPA-1-9 inhibited virus-induced cough. The water solubility of DIPA-1-9 facilitates its homogeneous dissolution in syrup for localized delivery to the pharyngeal surface. The volume of syrup times the concentration of DIPA-1-9 is equal to the dose. A dose of DIPA-1-9 of about 4 to 6 mg in 0.5 to 0.8 mL of syrup delivered to the base of the tongue will produce a robust, cooling sensation, without irritation and sting, and without unpleasant taste, lasting ≤5 min. The onset of drug action of ≤1 min. This immediate onset is surprising and unprecedented as there are no similar products on the market. The DIPA-1-9 sensory effect is sufficient to treat discomforts of the upper aerodigestive tract including: acute and chronic cough, mucus accumulation in the airways, dyspepsia, dysphagia, and dyspnea. In summary, DIPA-1-9 formulated in syrup and delivered in a volume of ≤51 mL to the base of the tongue is an ideal medication for reducing sensory discomfort of the upper aerodigestive tract in a subject in need of treatment.

I claim:

1. A method of treating coughing in a subject in need thereof, the method comprising topically administering, to the base of the subject's tongue, a liquid composition comprising a therapeutically effective amount of 1-[diisopropyl-phosphinoyl]-nonane.

2. The method of claim 1, wherein the concentration of 1-[diisopropyl-phosphinoyl]-nonane in the liquid composition is from 1 to 10 mg/ml.

3. The method of claim 2, wherein the volume of the liquid composition is from about 0.3 to 1.5 ml.

4. The method of claim 1, wherein the liquid composition is in the form of a syrup.

5. The method of claim 2, wherein the liquid composition is in the form of a syrup.

6. The method of claim 3, wherein the liquid composition is in the form of a syrup.

7. The method of claim 4, wherein the syrup comprises water and the 1-[diisopropyl-phosphinoyl]-nonane is dissolved therein.

8. The method of claim 5, wherein the syrup comprises water and the 1-[diisopropyl-phosphinoyl]-nonane is dissolved therein.

9. The method of claim 6, wherein the syrup comprises water and the 1-[diisopropyl-phosphinoyl]-nonane is dissolved therein.

10. The method of claim 7, wherein the syrup further comprises a flavoring agent.

11. The method of claim 8, wherein the syrup further comprises a flavoring agent.

12. The method of claim 9, wherein the syrup further comprises a flavoring agent.

13. The method of claim 1, wherein the liquid composition is an aqueous composition and the 1-[diisopropyl-phosphinoyl]-nonane is dissolved therein.

14. The method of claim 2, wherein the liquid composition is an aqueous composition and the 1-[diisopropyl-phosphinoyl]-nonane is dissolved therein.

15. The method of claim 3, wherein the liquid composition is an aqueous composition and the 1-[diisopropyl-phosphinoyl]-nonane is dissolved therein.

* * * * *